United States Patent
Parker et al.

(10) Patent No.: US 12,411,106 B2
(45) Date of Patent: Sep. 9, 2025

(54) METHODS FOR ELECTROSCOPIC IMAGING FOR ANALYSIS OF CELLS

(71) Applicant: LIFE TECHNOLOGIES CORPORATION, Carlsbad, CA (US)

(72) Inventors: Scott Parker, Madison, CT (US); Hannah Devyldere, Tangent, OR (US); John Donohue, Southbury, CT (US); Daisy Chilin, Los Angeles, CA (US)

(73) Assignee: Life Technologies Corporation, Carlsbad, CA (US)

( * ) Notice: Subject to any disclaimer, the term of this patent is extended or adjusted under 35 U.S.C. 154(b) by 502 days.

(21) Appl. No.: 18/050,152

(22) Filed: Oct. 27, 2022

(65) Prior Publication Data

US 2023/0125382 A1    Apr. 27, 2023

Related U.S. Application Data

(60) Provisional application No. 63/272,361, filed on Oct. 27, 2021.

(51) Int. Cl.
  *G01N 27/414* (2006.01)
  *G06T 5/70* (2024.01)
  *G06T 7/10* (2017.01)

(52) U.S. Cl.
  CPC .......... *G01N 27/4145* (2013.01); *G06T 5/70* (2024.01); *G06T 7/10* (2017.01); *G06T 2207/20224* (2013.01)

(58) Field of Classification Search
  CPC .. G06T 7/10; G01N 15/1031; G01N 33/4836; G01N 27/414
  See application file for complete search history.

(56) References Cited

U.S. PATENT DOCUMENTS

2005/0037438 A1   2/2005  Fromherz et al.
2010/0301398 A1*  12/2010  Rothberg ........... G01N 27/4145
                                                  257/253

(Continued)

FOREIGN PATENT DOCUMENTS

WO    WO-2022140174 A3    8/2022

OTHER PUBLICATIONS

Lehmann M., et al., "Non-invasive Measurement of Cell Membrane Associated Proton Gradients by Ion-Sensitive Field Effect Transistor Arrays for Microphysiological and Bioelectronical Applications," Biosensors and Bioelectronics, Jun. 1, 2000, vol. 15, No. 3-4, XP027368927, pp. 117-124. (Year: 2000).*

(Continued)

*Primary Examiner* — Stephen R Koziol
*Assistant Examiner* — Ashley L. Hytrek
(74) *Attorney, Agent, or Firm* — Carolyn Koenig

(57) ABSTRACT

Analyzing cells disposed on a sensor array surface of a ChemFET sensor array, may include flowing a solution having a step change in pH across the sensor array surface, wherein ChemFET sensors of the sensor array generate signals in response to the step change in pH to produce electroscopic image data. Multiple frames of the electroscopic image data are acquired during an acquisition time interval. Each frame corresponds to signal samples generated by the sensor array measured at a sampling time during the acquisition time interval. Each frame comprises pixels, wherein a given pixel in the frame corresponds to a signal sample from a given sensor in the sensor array. The electroscopic image data is segmented, based on characteristics of the signal samples, into cell regions corresponding to locations of the cells on the sensor array surface and background regions corresponding to areas on the sensor array having no cells.

20 Claims, 19 Drawing Sheets

(56) References Cited

U.S. PATENT DOCUMENTS

2012/0143531 A1\* 6/2012 Davey .............. G01N 33/48785
 73/40.5 R
2020/0088676 A1\* 3/2020 Hinz ................... C09D 189/00

OTHER PUBLICATIONS

Pourciel-Gouzy, M. L., Assié-Souleille, S., Mazenq, L., Launay, J., & Temple-Boyer, P. (2008). pH-ChemFET-based analysis devices for the bacterial activity monitoring. Sensors and Actuators B: Chemical, 134(1), 339-344. (Year: 2008).\*

Lehmann M., et al., "Non-invasive Measurement of Cell Membrane Associated Proton Gradients by Ion-Sensitive Field Effect Transistor Arrays for Microphysiological and Bioelectronical Applications," Biosensors and Bioelectronics, Jun. 1, 2000, vol. 15, No. 3-4, XP027368927, pp. 117-124.

PCT/US2022/078760, International Search Report and Written Opinion, Feb. 28, 2023, 14 pages.

\* cited by examiner

Table 1

| Device | Pixels per Device | Pitch (μm) | Pixel Size (μm x μm) | Pixel Area μm²/pixel | FR max per Device (fps) | FR max per Row (fps) |
|---|---|---|---|---|---|---|
| A | 20M | 3.36 | 2.910 x 3.360 | 9.78 | 240 | 75,000 |
| B | 40M | 3.36 | 2.910 x 3.360 | 9.78 | 120 | 75,000 |
| C | 165M | 1.68 | 1.453 x 1.680 | 2.44 | 30 | 75,000 |
| D | 300M | 1.26 | 1.093 x 1.262 | 1.38 | 30 | 162,000 |
| E | 660M | 0.85 | 0.733 x 0.846 | 0.62 | 15 | 162,000 |

FIG. 2B

| Cell Size | Device | Pitch (µm) | Pixel Size (µm x µm) | Pixel Area µm²/pixel | Pixel per Cell Area | % Pixel Coverage | Rows per Cell ID | FR$_{max}$ per Row (fps) | FR$_{max}$ per Row$_{Cell\ ID}$ (fps) |
|---|---|---|---|---|---|---|---|---|---|
| Extra large $\bar{D}$ = 100 µm $\bar{A}$ = 7854 µm² | Chip 1 | 3.36 | 2.910 x 3.360 | 9.78 | 803 | 0.1% | 30 | 75,000 | 2,500 |
| | Chip 2 | 1.68 | 1.453 x 1.680 | 2.44 | 3,219 | 0.03% | 60 | 75,000 | 1,250 |
| | Chip 3 | 1.26 | 1.093 x 1.262 | 1.38 | 5,691 | 0.02% | 79 | 162,000 | 2,051 |
| | Chip 4 | 0.85 | 0.733 x 0.846 | 0.62 | 12,668 | 0.008% | 118 | 162,000 | 1,373 |
| Large $\bar{D}$ = 50 µm $\bar{A}$ = 1964 µm² | Chip 1 | 3.36 | 2.910 x 3.360 | 9.78 | 201 | 0.5% | 15 | 75,000 | 5,000 |
| | Chip 2 | 1.68 | 1.453 x 1.680 | 2.44 | 805 | 0.1% | 30 | 75,000 | 2,500 |
| | Chip 3 | 1.26 | 1.093 x 1.262 | 1.38 | 1,423 | 0.07% | 40 | 162,000 | 4,050 |
| | Chip 4 | 0.85 | 0.733 x 0.846 | 0.62 | 3,168 | 0.03% | 59 | 162,000 | 2,746 |
| Medium $\bar{D}$ = 25 µm $\bar{A}$ = 491 µm² | Chip 1 | 3.36 | 2.910 x 3.360 | 9.78 | 50 | 0.2% | 7 | 75,000 | 10,714 |
| | Chip 2 | 1.68 | 1.453 x 1.680 | 2.44 | 201 | 0.5% | 15 | 75,000 | 5,000 |
| | Chip 3 | 1.26 | 1.093 x 1.262 | 1.38 | 356 | 0.2% | 20 | 162,000 | 8,100 |
| | Chip 4 | 0.85 | 0.733 x 0.846 | 0.62 | 792 | 0.1% | 29 | 162,000 | 5,587 |
| Small $\bar{D}$ = 10 µm $\bar{A}$ = 78 µm² | Chip 1 | 3.36 | 2.910 x 3.360 | 9.78 | 8 | 12% | 3 | 75,000 | 25,000 |
| | Chip 2 | 1.68 | 1.453 x 1.680 | 2.44 | 32 | 3% | 6 | 75,000 | 12,500 |
| | Chip 3 | 1.26 | 1.093 x 1.262 | 1.38 | 56 | 2% | 8 | 162,000 | 20,250 |
| | Chip 4 | 0.85 | 0.733 x 0.846 | 0.62 | 126 | 0.8% | 12 | 162,000 | 13,500 |
| Very Small $\bar{D}$ = 5 µm $\bar{A}$ = 20 µm² | Chip 1 | 3.36 | 2.910 x 3.360 | 9.78 | 2 | 50% | 1 | 75,000 | 75,000 |
| | Chip 2 | 1.68 | 1.453 x 1.680 | 2.44 | 8 | 12% | 3 | 75,000 | 25,000 |
| | Chip 3 | 1.26 | 1.093 x 1.262 | 1.38 | 14 | 7% | 4 | 162,000 | 40,500 |
| | Chip 4 | 0.85 | 0.733 x 0.846 | 0.62 | 32 | 3% | 6 | 162,000 | 27,000 |

FIG. 2C $$\begin{matrix} 1 & \cdots & 1 & 1 & 1 & \cdots & 1 \\ \vdots & \ddots & \vdots & \vdots & \vdots & \iddots & \vdots \\ 1 & \cdots & 1 & 0 & 1 & \cdots & 1 \\ \vdots & \iddots & \vdots & \vdots & \vdots & \ddots & \vdots \\ 1 & \cdots & 1 & 1 & 1 & \cdots & 1 \end{matrix}$$

FIG. 5

METHODS FOR ELECTROSCOPIC IMAGING FOR ANALYSIS OF CELLS

CROSS-REFERENCE TO RELATED APPLICATIONS

This application claims the benefit under 35 U.S.C. § 119(e) of U.S. Provisional Application No. 63/272,361, filed Oct. 27, 2021. The entire contents of the aforementioned application are incorporated by reference herein.

SUMMARY

A method for analyzing cells disposed on a sensor array surface of a ChemFET sensor array device, may include flowing a solution having a step change in pH across the sensor array surface, wherein a plurality of ChemFET sensors of the ChemFET sensor array generate a plurality of signals in response to the step change in pH of the flowed solution to produce electroscopic image data; acquiring multiple frames of the electroscopic image data during an acquisition time interval, wherein each frame corresponds to signal samples of the plurality of signals generated by the ChemFET sensor array measured at a sampling time during the acquisition time interval, wherein each frame comprises a plurality of pixels, wherein a given pixel in the frame corresponds to a signal sample from a given sensor in the ChemFET sensor array; and segmenting the electroscopic image data into one or more cell regions corresponding to locations of the cells on the sensor array surface and one or more background regions corresponding to areas on the sensor array having no cells based on characteristics of the signal samples generated response to the step change in pH of the flowed solution.

BRIEF DESCRIPTION OF THE DRAWINGS

The novel features are set forth with particularity in the appended claims. A better understanding of the features and advantages of the present teachings will be obtained by reference to the following detailed description that sets forth illustrative embodiments, and the accompanying drawings of which:

FIG. 2B is a table summarizing attributes of exemplary ChemFET sensors.

FIG. 2C is a table of displaying ChemFET system attributes for cell analysis across a range of cell sizes.

FIG. 5 gives an example (not to scale) of a convolutional kernel that could be used to calculate a local spatial average of pixel values.

DETAILED DESCRIPTION

Electroscopic imaging of cells using a ChemFET sensor array-based system may include plating a sample of cells on a sensor array surface of a ChemFET sensor array device mounted in a flow cell. Each cell in the sample of cells has a footprint over the sensor array surface. During an experiment on the sample of cells, the ChemFET sensor array-based system is configured to output a signal for each sensor in the ChemFET sensor array. The output signal for each sensor is sampled at instants in time by an analog-to-digital converter. The sampled signals for the ChemFET sensor array at a particular instant in time may be represented as a two-dimensional electroscopic image.

Figure 1A:
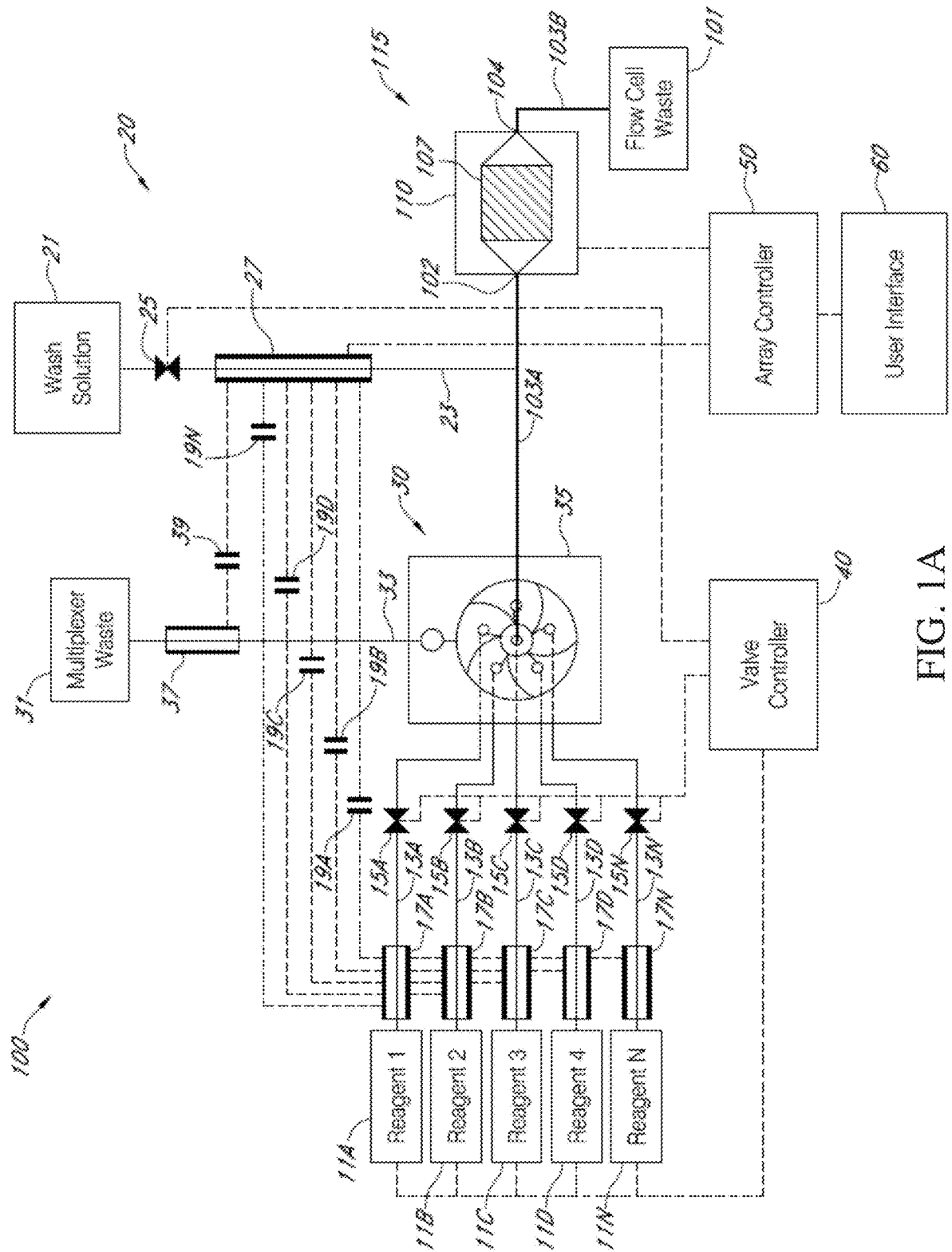
FIG. 1A is a block diagram depicting a chemical field effect transistor (ChemFET)-based cell analysis system that produces electroscopic images, according to various embodiments of systems and methods of the present teachings.

FIG. 1A illustrates generally a block diagram of exemplary components of cell analysis system 100 according to the present teachings. As depicted in FIG. 1A, cell analysis system 100 can include various fluidic systems, as well as array controller 50, user interface 60, and sensor array device assembly 115. As will be described in more detail herein, various cell analyses can be performed using sensor array device 110 of sensor array device assembly 115. The structure and/or design of a cell analysis system for use with the present teachings may include one or more features described in U.S. Pat. Appl. Publ. No. 2020/0088676, Mar. 19, 2020, incorporated by reference herein in its entirety.

Figure 1B:
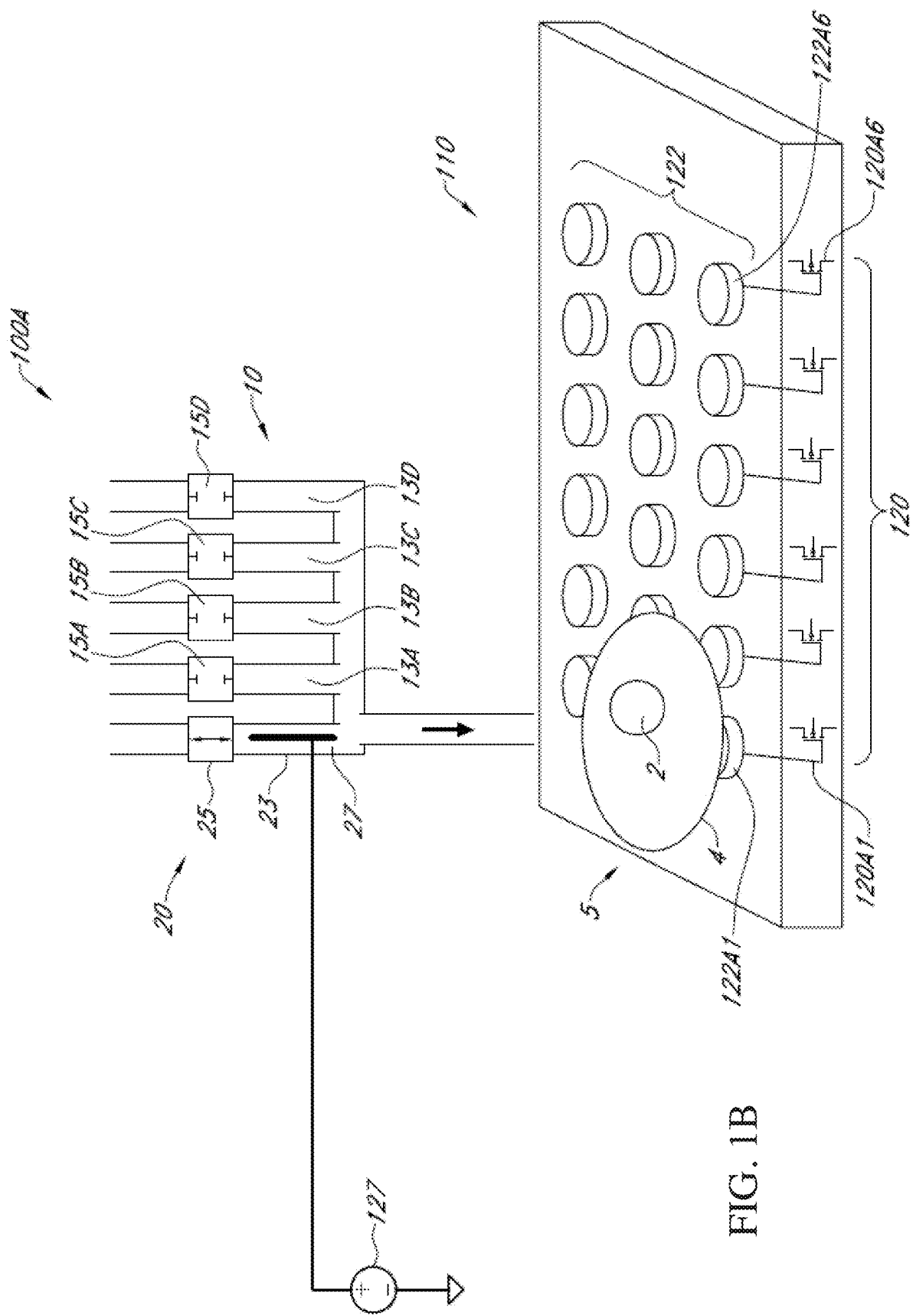
FIG. 1B is a schematic depiction of a cell positioned on a cell analysis system of the present teachings.

FIG. 1B illustrates generally a graphic depiction of cell analysis system 100A. As depicted in FIG. 1B cell 5, with nucleus 2 and cell membrane 4, is positioned over a plurality of a subset of microwells, thereby defining an area of contact or footprint that cell 5 occupies over a corresponding subset of sensors. As recited herein, "area of contact" and "footprint" can be used interchangeably. Cell analysis system 100A shares many of the same features as described for the schematic depiction of cell analysis system 100 of FIG. 1A. Cell analysis system 100A of FIG. 1B can include reagent fluidic system 10 and wash solution fluidic system 20. Reagent fluidic system 10 can include a plurality of reagent containers, such as reagent containers 11A-11D of FIG. 1B. Each reagent container can be in fluid communication with a reagent fluid line, such as reagent fluid lines 13A-13D, of FIG. 1B. Flow from each reagent fluid line of a cell analysis system of the present teachings can be controlled by a valve, such as reagent fluid line valves 15A-15D of FIG. 1B. Wash solution fluidic system 20 can include wash solution container 21, which can contain a wash solution of known electrolyte composition, as well as wash solution fluid line 23, wash solution fluid line valve 25, and reference electrode 27 in wash solution fluid line 23. As will be described in more detail herein, reference electrode 27 can provide a stable reference voltage 127 for sensor in a sensor array device. As such, sensor array device 110 of FIG. 1B can be in fluid communication with reagent fluidic system 10 and wash solution fluidic system 20. Though not shown in FIG. 1B, an additional electrode that can be in communication with the sensor array device can be utilized to provide an electrical stimulus to cells on a sensor array, such as cell 5 of FIG. 1B.

Sensor array device 110 can include sensor array or pixel array 120. As recited herein, the terms "sensor" and "pixel," as well the terms "device" and "chip" and derivatives of these terms can be used interchangeably. Additionally, "sensor array" and "ChemFET sensor array," and derivatives thereof can be used interchangeably. Though depicted in FIG. 1B as regular array two-dimensional array, various embodiments of sensor arrays of the present teachings can be arranged in a variety of array geometries, for example, in a hexagonal closest packed geometry. Sensor array device 110 can include a microwell array 122, which as illustrated in FIG. 1B, depicts each microwell cooperatively engaged with each sensor or pixel in sensor array 120, so that each microwell 122A1 through microwell 122A6 is cooperatively engaged with a corresponding sensor 120A1 through sensor 120A6. However, for various embodiments of sensor array devices of the present teachings, there can be more than one pixel per well. As will be described in more detail herein, various types of sensor array devices of the present teachings can be fabricated with a defined but different microwell depth. Still other types of sensor array devices of the present teachings may have no microwell structures formed over the sensor array. Each sensor of sensor array 120 can have a sensing surface in fluidic communication with the fluid in the microwell array 122. For various embodiments of cell analysis system 100 of the present teachings, each sensor of sensor array 120 can be a chemical field-effect transistor (ChemFET), where each sensor in senor array 120 includes at least one chemically-sensitive field-effect transistor. According to the present teachings sensor array 120 can include ChemFETs that can be fabricated with sensing surfaces modified to be selective for the analysis of a targeted chemical species of interest for cell biology, for example, such as glucose, sucrose, lactate and urea. By way of another non-limiting example, ion sensitive field-effect transistors (ISFETs) can have sensing surfaces modified to be selective for various ions of interest; particularly for various cell metabolism studies, such as hydrogen, potassium, calcium and chloride.

In that regard, the present inventors have recognized that various embodiments of cell analysis systems of the present teachings can be used to monitor changes in, for example, cell electrophysiology and metabolism for cells subjected to any of a variety of conditions or stimuli. Moreover, the present inventors have recognized that any change in the state of a cell that can cause a change in potential of a sensing surface of a ChemFET sensor can be monitored by sensors of various embodiments of a ChemFET sensor array of the present teachings. For example, the present inventors have recognized that a cell is capacitively coupled to the sensing surface of a sensor, so that as the electrical potential across a cell membrane changes in response to a chemical or electrical stimulus, the changing electrical potential across the cell membrane can be detected by sensors of various embodiments of a ChemFET sensor array of the present teachings. Additionally, any change, for example, in cell metabolism that can cause a change in potential of the sensing surface of a ChemFET sensor can be detected by sensors of various embodiments of a ChemFET sensor array of the present teachings. As will be described in more detail herein, such changes can be locally detected in association with an area of contact or footprint of a cell anchored on a sensor array surface or can be detected in areas not associated with a cell footprint, for example, such as for cellular efflux that may stream from a cell in response to a condition or stimulus.

Data collected in experiments monitoring cellular response to various stimuli with various embodiments of ChemFET sensor array devices of the present teachings can be presented to an end user in a number of formats. In one format, temporal response is presented as detector counts that can be readily correlated to millivolt (mV) change in sensing surface potential as a function of time. In another format, for any of a selected time over a course of a selected application, a spatial visualization of cells can be presented as an electroscopic image. The present inventors have recognized that as electroscopic imaging is predicated on a variety of responses that can be elicited for living cells, it can useful, for example, as a general tool for visualizing cells on a sensor array. For example, by reviewing an electroscopic image of cells anchored on a sensor array, an end-user can select an area of interest as part of application configuration before running an experiment. As will be described in more detail herein, windowing down a selected area of a sensor array device thereby increases the data rate for the experiment. According to the present teachings, the substantial pixel coverage over a footprint of a cell coupled with high data rate can provide subcellular monitoring of, for example, action potential of various excitable cells for which a data rate in the sub-millisecond range may be required.

Figure 1C:
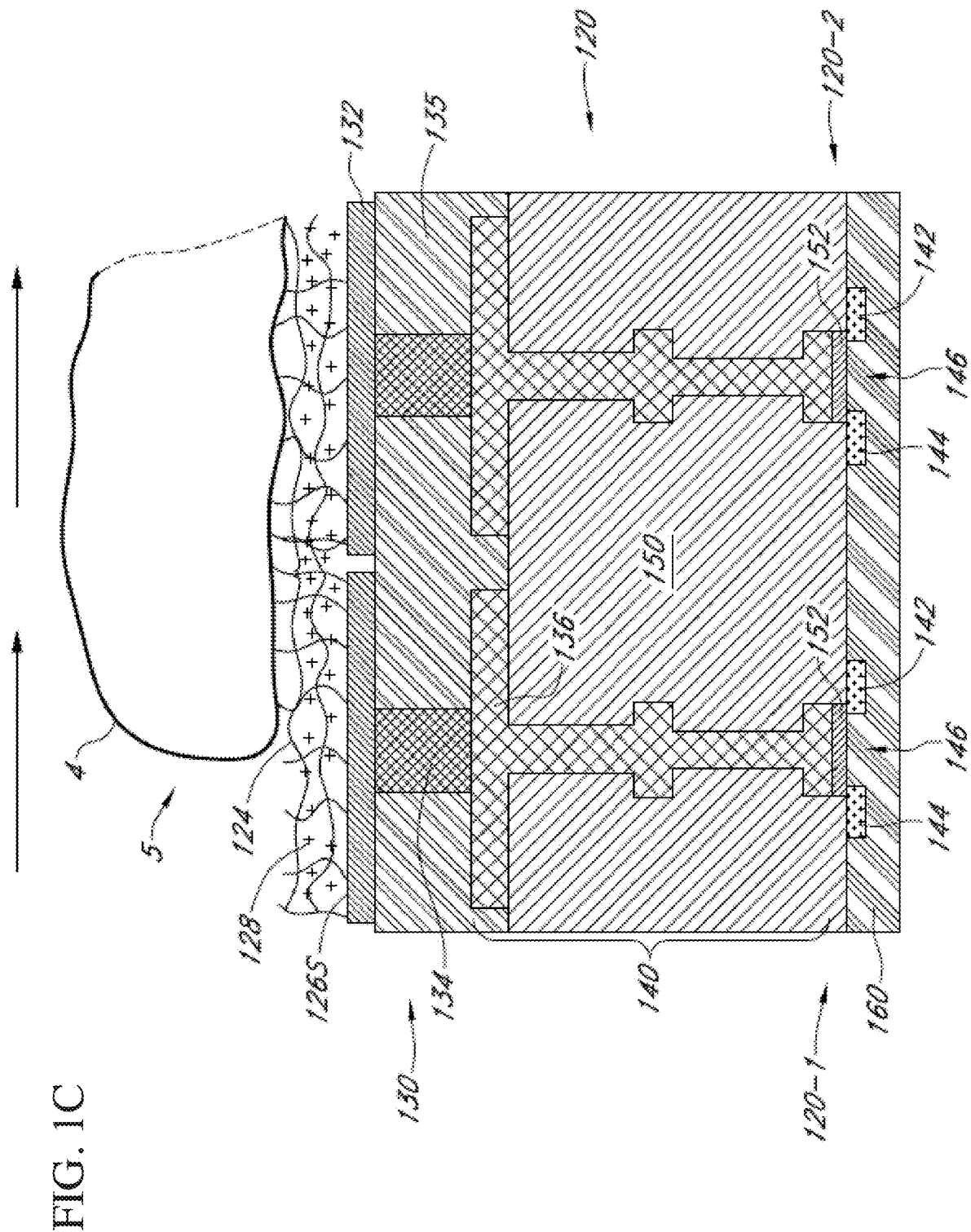
FIG. 1C is a schematic section view of a cell positioned on a sensor device of the present teaching.

In FIG. 1C, a partial section view of sensor array 120 is depicted with first sensor 120-1 and second sensor 120-2. In various embodiments of a sensor array device of the present teachings, sensor array 120 can include floating gate upper portion 130 coupled to sensor floating gate structure 140. Alternatively, for various embodiments of a sensor array device of the present teachings, sensor array 120 can include sensor floating gate structure 140. As will be described in more detail herein, floating gate upper portion 130 can include a top metal layer, sensor plate 132, as well as metal via 134, formed in dielectric 135.

Sensor floating gate structure 140 can have metal layer 136 coupled to sensor plate 132 through metal via 134. Metal layer 136 is the uppermost floating gate conductor in sensor floating gate structure 140. In the illustrated example, sensor floating gate structure 140 includes multiple layers of conductive material within layers of dielectric material 150. Sensors 120-1 and 120-2 can include conduction terminals including source/drain region 142 and source/drain region 144 within semiconductor substrate 160. Source/drain region 142 and source/drain region 144 comprise doped semiconductor material having a conductivity of a type different from the conductivity type of substrate 160. For example, source/drain region 142 and source/drain region 144 can comprise doped P-type semiconductor material, and substrate 160 can comprise doped N-type semiconductor material. Channel region 152 separates source/drain region 142 and source/drain region 144. Floating gate structure 140 overlies channel region 146, and is separated from substrate 160 by gate dielectric 152. Gate dielectric 152 can be silicon dioxide, for example. Alternatively, other suitable dielectrics can be used for gate dielectric 152 such as, for example materials with higher dielectric constants, silicon carbide (SiC), silicon nitride (Si3N4), silicon oxynitride ($Si_2N_2O$), aluminum nitride (AlN), hafnium dioxide (HfO2), tin oxide (SnO2), cesium oxide (CeO2), titanium oxide (TiO2), tungsten oxide (WO3), aluminum oxide (Al2O3), lanthanum oxide (La2O3), gadolinium oxide (Gd2O3), and any combination thereof.

As will be described in more detail herein, sensing surface 126S of sensor plate 132 can act as the sensor surface for monitoring changes in, for example, cell electrophysiology and metabolism for cells subjected to any of a variety of conditions or stimuli. In that regard, cell 5 shown in FIG. 1C as a partial section of a cell, is depicted as positioned over sensor plate 132 of sensors 120-1 and 120-2. Cell 5 is depicted as anchored to sensor array 120 via surface coating 124. Surface coating 124 can be any cell-compatible material, such as various biopolymer materials including poly-D-lysine, laminin, fibronectin, collagen, and combinations thereof, as well as various preparations of extracellular matrix (ECM). An end user can run applications using cell analysis systems of the present teachings that controllably flow various reagents and solutions can over the surface of sensor array 120, as indicated by the arrows at the top of FIG. 1C.

Sensors 120-1 and 120-2 are responsive to changes in the surface potential of ion layer 128 proximate to sensing surface 126S, which can cause changes in the voltage on floating gate 140. As such, an applied reference voltage, as previously described herein for FIG. 1B, ensures that the voltage of the floating gate exceeds a threshold voltage, providing that small changes in the floating gate voltage can cause current to flow through channel region 146, resulting in an output signal for sensors 120-1 and 120-2. In that regard, changes to the surface potential of ion layer 128 can be measured by measuring the current in channel region 146 between, for example, source region 142 and drain region 144. As such, sensors 120-1 and 120-2 can be used directly to provide a current-based output signal on an array line connected to source region 142 or drain region 144, or indirectly with additional circuitry to provide a voltage-based output signal.

As described herein, any change in the state of cell 5 that can alter the surface potential in ion layer 128 can be monitored by various embodiments of ChemFET sensor array devices of the present teachings. With respect to output signal, any cell activity that can increase surface potential would result in an output signal of positive amplitude for a ChemFET sensor, while any cell activity that can decrease surface potential would result in an output signal of negative amplitude for a ChemFET sensor. In that regard, any change in the state of a cell that can change the surface potential of a ChemFET sensor can result in a measurable output signal. For example, any metabolic activity that can increase ion concentration of a cationic species which an ISFET sensor is selective for would cause an increase in surface potential. The result would be an output signal of positive amplitude for that ISFET sensor. Conversely, any metabolic activity that can decrease ion concentration of a cationic species for which an ISFET sensor is selective for would cause a decrease in surface potential. The result would be an output signal of negative amplitude for that ISFET sensor. In another example, the surface potential can be altered by the capacitive coupling of cell 5 to sensor array 120, so that as the electrical potential across cell membrane 4 changes in response to a chemical or electrical stimulus, the changing electrical potential across the cell membrane can be detected by ChemFET sensors 120-1 and 120-2.

Figure 2A:
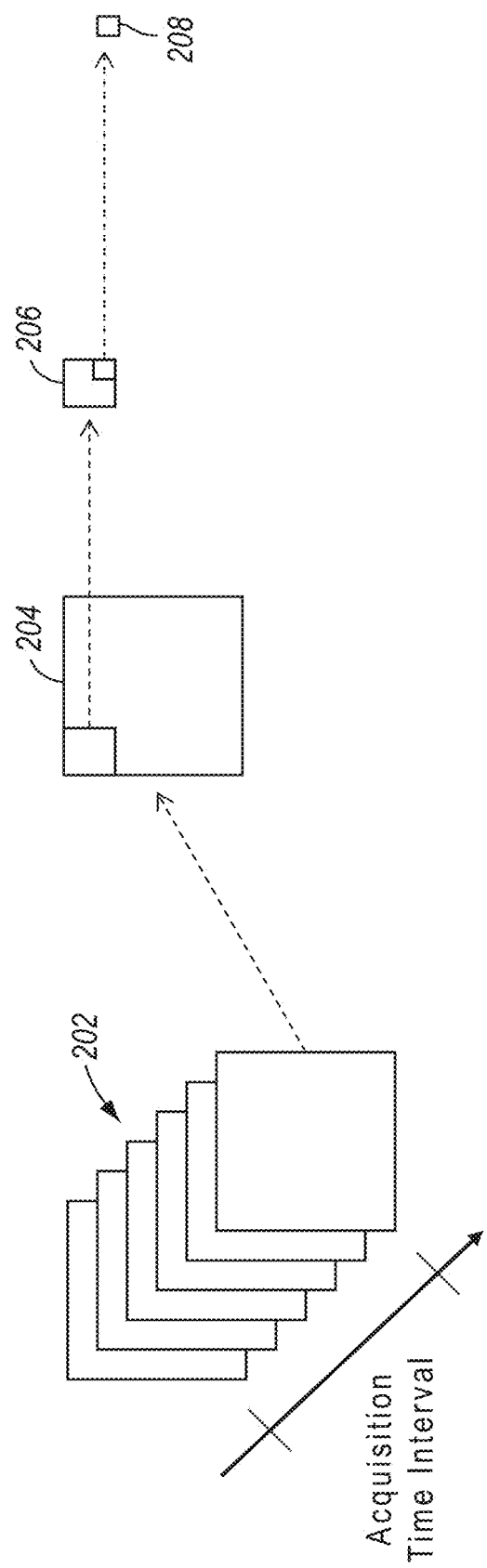
FIG. 2A illustrates an example the output signals from the sensor array during an acquisition time interval represented as a sequence of 2D images.

The output signals from the sensor array over an acquisition time interval may be represented as a sequence of two dimensional (2D) images, where each image corresponds to the array of signal samples received from the sensor array at a given time, similar to a movie. FIG. 2A illustrates an example of representing output signals from the sensor array during an acquisition time interval as a sequence of 2D images 202. The 2D image 204 at a particular sampling time may be referred to herein as a frame, analogous to a frame of a movie or video. Each 2D image is referred to herein as an electroscopic image. Each 2D image 204 may comprise plurality of tiles 206 and a plurality of pixels 208. Since a frame is produced at each sampling time, the terms "sampling time" and "frame time" are used interchangeably herein. For example, 15 frames per second (fps) may be acquired during an acquisition time interval. For an acquisition interval of 7 seconds, 105 frames would be acquired in each acquisition time interval. Exemplary dimensions are 640×664 pixels for a tile and 8 tiles by 12 tiles may comprise an entire image for the frame. In some embodiments, the tiles may correspond to physical tiles of the ChemFET sensor array, where the physical tiles have dimensions of approximately 2 mm by 2 mm.

FIG. 2B shows Table 1 that summarizes attributes of exemplary ChemFET sensors. Various embodiments of a sensor array device of the present teachings can have between about 20M to about 660M pixels, with a center-to-center spacing between each sensor; or the pitch, of between about 850 nm to about 3.36 μm. With respect to data collection, a collection of sensor output signals from all sensors in an array constitutes a frame of data. For various sensor array devices of the present teachings with between about 20 million pixels to about 660 million pixels, a frame of is a data file of substantial size, which is collected in units of hertz (Hz) as frames per second. Further, there is an inverse relationship between an area of interest selected representing the number of pixels and the rate at which data can be collected, so that by selecting a smaller subset of pixels to monitor, i.e. by windowing down the area of a sensor array device over which data is collected, frame rate can be increased. The impact of windowing down is evidenced in Table 1 by comparison of the values entered in the second to last column, which is maximum frame rate for collecting data from an entire device, to the values entered into the last column, which is maximum frame rate for collecting data from a single row of a device. As such, by windowing down to collect data from a single row, frame rate is substantially increased.

Additionally, as provided in Table 1, the only difference between Device A and Device B is the number of total sensors per device, in which there are double the number of sensors per Device A versus Device B. As shown in Table 1, the frame rate for Device B is half that of Device A, consistent with an inverse relationship between number of pixels and the rate at which data can be collected. As such, a device with a desirable frame rate matched to an application can be selected.

FIG. 2C shows a table that summarizes attributes for exemplary sensor array devices for cell analysis. Sensor array device attributes that can be varied to provide a variety of sensor array devices of the present teachings include pixel dimensions, as well as the rate at which data can be collected from a sensor array device. FIG. 2C provides an overview of five categories of cells by size in relationship to four exemplary sensor array devices of varying sensor (pixel) dimensions, as given in Table 1 for Device B through Device E. The five categories of cells are identified descriptively, as well as by average diameter and average footprint.

By inspection of FIG. 2C, for a very small cell anchored on a sensor array surface with an average diameter of 5 μm and average area of 20 μm$^2$, a minimum area of contact or footprint corresponds to about 1 row and about 2 pixels for a Chip 1 device, which increases to 6 rows and 32 pixels for a Chip 4 device. Similarly, for a small cell anchored on a sensor array surface with an average diameter of 10 μm and average area of 78 μm$^2$, a minimum area of contact or footprint corresponds to about 3 rows and about 8 pixels for a Chip 1 device, which increases to 12 rows and 126 pixels for a Chip 4 device. For a medium cell anchored on a sensor array surface with an average diameter of 25 μm and average area of 491 μm$^2$, a minimum area of contact or footprint corresponds to about 7 rows and about 50 pixels for a Chip 1 device, which increases to 29 rows and 792 pixels for a Chip 4 device. Large cells anchored on a sensor array surface with an average diameter of 50 μm and average area of 1,964 μm$^2$, can have a minimum area of contact or footprint corresponding to about 15 rows and about 201 pixels for a Chip 1, which increases to 59 rows and 3,168 pixels for a Chip 4 device. Finally, for an extra large cell anchored on a sensor array surface with an average diameter of 100 μm and average area of 7,854 μm$^2$, a minimum area of contact or footprint corresponds to about 30 rows and about 803 pixels for a Chip 1 device, which increases to 118 rows and 12,668 pixels for a Chip 4 device. From inspection of FIG. 2C, the trend is towards increasing pixel coverage with increasing cell size and decreasing pixel size.

From a pixel perspective, the column of percent pixel coverage is the percentage of area of a cell that a single pixel covers. For a very small cell anchored on a sensor array surface, a single pixel corresponds to 50% coverage for a Chip 1 device, whereas for a Chip 4 device a single pixel corresponds to 3% coverage. Similarly, for a small cell anchored on a sensor array surface, a single pixel corresponds to 12% coverage for a Chip 1 device, whereas for a Chip 4 device a single pixel corresponds to 0.8% coverage. For a medium cell anchored on a sensor array surface, a single pixel corresponds to 2% coverage for a Chip 1 device, whereas for a Chip 4 device a single pixel corresponds to 0.1% coverage. Large cells anchored on a sensor array surface can have a single pixel corresponding to 0.5% coverage for a Chip 1 device, whereas for a Chip 4 device a single pixel corresponds to 0.03% coverage. Finally, for an extra large cell anchored on a sensor array surface, a single pixel corresponds to 0.1% coverage for a Chip 1 device, whereas for a Chip 4 device a single pixel corresponds to 0.008% coverage. From inspection of FIG. 2C, the trend is towards decreasing percentage of cell coverage per pixel with increasing cell size and decreasing pixel size.

Given what is presented in the table of FIG. 2C, selection of pixel coverage for exemplary sensor array devices of the present teaching can be made for a variety of average cell diameters. For example, for cells from about 5 μm to about 100 μm, a selection of sensor array devices can be made to provide coverage from about 8 pixels over 3 rows of pixels to about 12,668 pixels over 118 rows of pixels for a corresponding footprint of a cell anchored on a sensor array surface. Over that range of cell sizes, pixel sizes can vary, so that each pixel of a selected sensor array device can cover from between about 12% of a cell to about 0.008% of a cell. Based on the data presented in FIG. 2C, it is clear that for any cell size, an exemplary sensor array device can be selected that can provide a substantial number of sensors associated with an area of contact that a cell can occupy on a sensor array device. The spatial resolution that can be provided by various sensor array devices of the present teachings can allow for subcellular discrimination of signals; hence providing for subcellular analysis.

With respect to data collection, for various cell analysis systems of the present teachings, a collection of sensor output signals from all sensors in an array constitutes a frame of data. Given that various sensor array devices of the present teachings can have between about 20 million pixels to about 660 million pixels, a frame of data from various sensor array devices of the present teachings is a data file of substantial size. Additionally, various cell analysis systems of the present teachings include control circuitry coupled to a sensor array device that is configured to generate a substantial number of frames of data from a sensor array device every second. Moreover, there is an inverse relationship between an area of interest selected and the rate at which data can be collected, so that by selecting a smaller subset of pixels to monitor, i.e. by windowing down the area of a sensor array device over which data is collected, frame rate can be increased.

For example, in reference to Table 1, a sensor array device with 40 million pixels can collect data at a frame rate of about 120 frames per second (fps). Then, if an area of interest of 20 million pixels is selected, data at a frame rate of about 240 frames per second (fps) can be collected, and for an area of interest of a single sensor array row is selected, data at a frame rate of about 75,000 frames per second (fps) can be collected. Specifically, with respect to exemplary sensor array devices of the present teachings presented in FIG. 2C, the maximum frame rate per row of sensors is provided in the second-to-last column. In the last column, the maximum frame rate that data can be collected for a fractional portion of rows covered by a cell is presented, as derived by a dividing maximum frame rate per row by rows per cell diameter.

As can be seen by inspection of the last column of FIG. 2C, a substantial number of frames per second can be collected for targeted areas of interest across a range of cell sizes, providing for data collection comfortably within the kHz range. For a very small cell anchored on a sensor array surface, data can be collected at a maximum frame rate of 75,000 fps for a Chip 1 device, whereas for a Chip 4 data can be collected at a maximum frame rate of 27,000 fps.

Similarly, for a small cell anchored on a sensor array surface, data can be collected at a maximum frame rate of 25,000 fps for a Chip 1 device, whereas for a Chip 4 data can be collected at a maximum frame rate of 13,500 fps. For a medium cell anchored on a sensor array surface, data can be collected at a maximum frame rate of 10,714 fps for a Chip 1 device, whereas for a Chip 4 data can be collected at a maximum frame rate of 5,587 fps. Large cells anchored on a sensor array surface can have a maximum frame rate of 5,000 fps for a Chip 1 device, whereas for a Chip 4 data can be collected at a maximum frame rate of 2,746 fps. Finally, for an extra large cell anchored on a sensor array surface data can be collected at a maximum frame rate of 2,500 fps for a Chip 1 device, whereas for a Chip 4 data can be collected at a maximum frame rate of 1,373 fps.

From inspection of FIG. 2C, the trend is towards decreasing frame rate with increasing cell size and decreasing pixel size, which is consistent with the inverse relationship between an area of interest selected and the rate at which data can be collected. As such, by selecting a smaller subset of pixels to monitor, i.e. by windowing down the area of a sensor array device over which data is collected, frame rate can be increased. Additionally, in reference to Table 1, a device with a desirable frame rate matched to an application can be selected.

Figure 3:
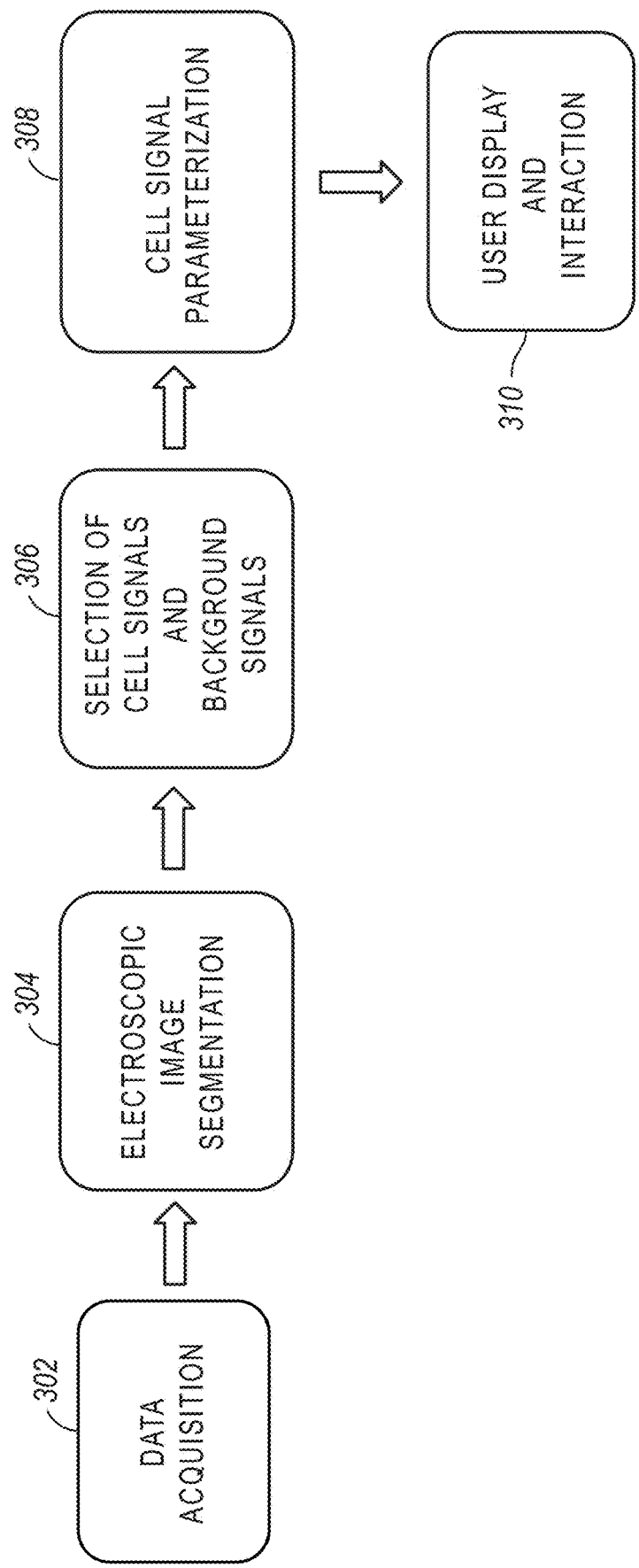
FIG. 3 is a block diagram giving a high level overview of processing electroscopic image data, in accordance with an embodiment.

FIG. 3 is a block diagram giving a high level overview of processing electroscopic image data, in accordance with an embodiment. Electroscopic image data comprise a sequence of two-dimensional images 202 acquired from the sensor array over an acquisition time interval. In an example, the time interval may be 7 seconds in length. The acquisition time intervals may be separated by pause intervals. The pause interval may allow for data transfer of the electroscopic image data from the sensor array to the system processor. In some embodiments, the pause interval may be part of the experimental design. For example, the experiment may acquire high-speed data at periodical intervals separated by pause intervals. For example, the experiment may acquire 7 seconds of 120 fps data and have a pause interval of 5 minutes in order to sample fast transient activity over longer periods of time. The data acquisition step 302 may acquire electroscopic image data comprising signal samples from the individual sensors of the sensor array in parallel for each sampling time of the acquisition time interval. The data acquisition step 302 may acquire electroscopic image data over one or more acquisition time intervals to produce one or more sequences of electroscopic images. The one or more sequences of electroscopic images may be stored in a memory for analysis by the processor.

The data acquisition step 302 may include receiving electroscopic image data from the sensor array in response to a "CellFind" flow. A CellFind flow may comprise a solution which has a specific pH step difference from the buffered media used to coat the sensor array surface on which the sample of cells is deposited. For example, the buffered media may have a pH in the range of 4 to 8 units. For example, Thermo Fisher Live Cell Imaging Solution (Thermo Fisher Scientific, Cat. No. A14291DJ) may be used for the buffered media. In order to achieve a specific pH difference for the CellFind flow, a small amount of NaOH or HCl is added to adjust the pH of the solution. The solution with the pH step difference is flowed across the sensor array. For example, the solution may have a pH difference of 0.01 to 0.5 units. The Cellfind solution is adjusted relative to the media, and could be either acidic or basic, relative to the buffered media. For example, the pH change may be from 7.4 in the buffered media to 7.3 in CellFind flow solution. The pH change may be positive or negative. The ChemFET sensors generate a signal in response to the change in pH. In some embodiments, the polarity of the measured signal may be changed so that the response is in the positive direction, even if the pH step change is in the negative direction. Regions of the sensor array not covered with cells will respond more quickly to the pH step difference. Regions of the sensor array surface covered with one or more cells will have a slower response to the pH step difference in the CellFind flow due to occlusion of the sensors by the cells. The data acquisition during one or more acquisition time intervals occurring after the CellFind flow provides electroscopic image data over time showing dynamic changes related to the locations of cells.

Figure 6A:
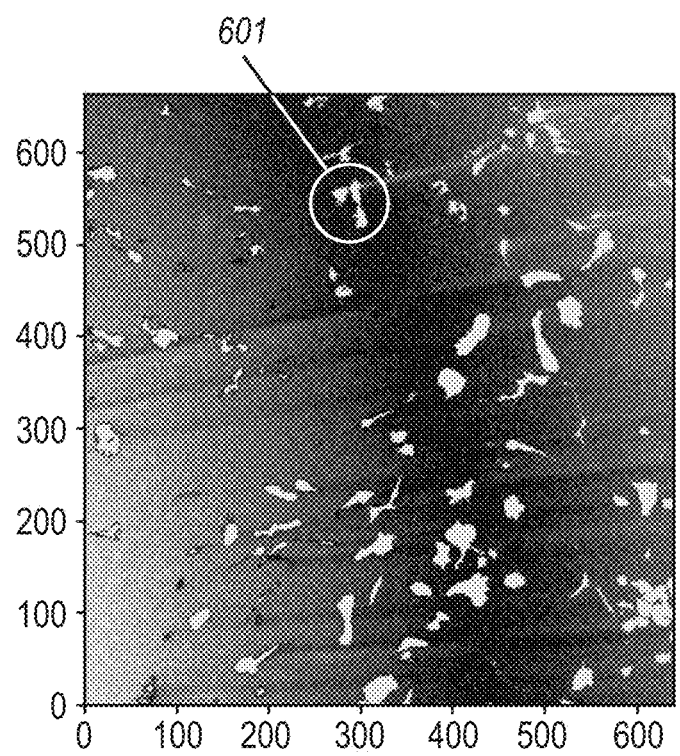
FIG. 6A shows an example of a grayscale image of a tile in response to a CellFind flow.
Figure 6B:
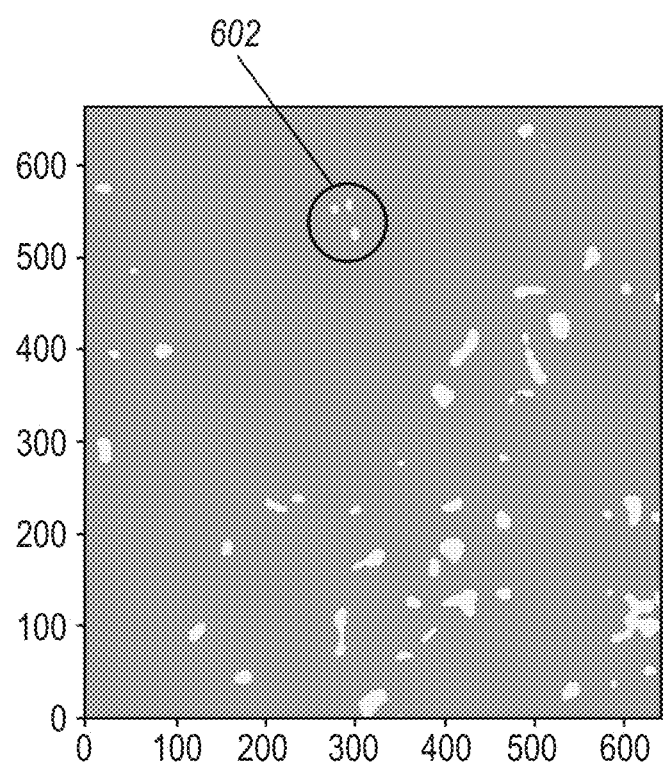
FIG. 6B shows an example of a coarse cell mask for a tile.
Figure 6C:
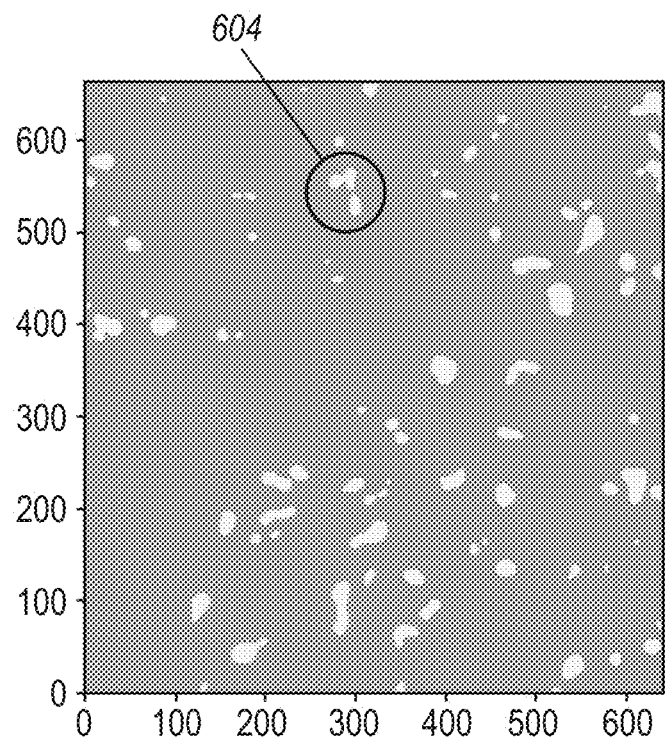
FIG. 6C shows an example of a tile of a local background corrected cell mask.
Figure 6D:
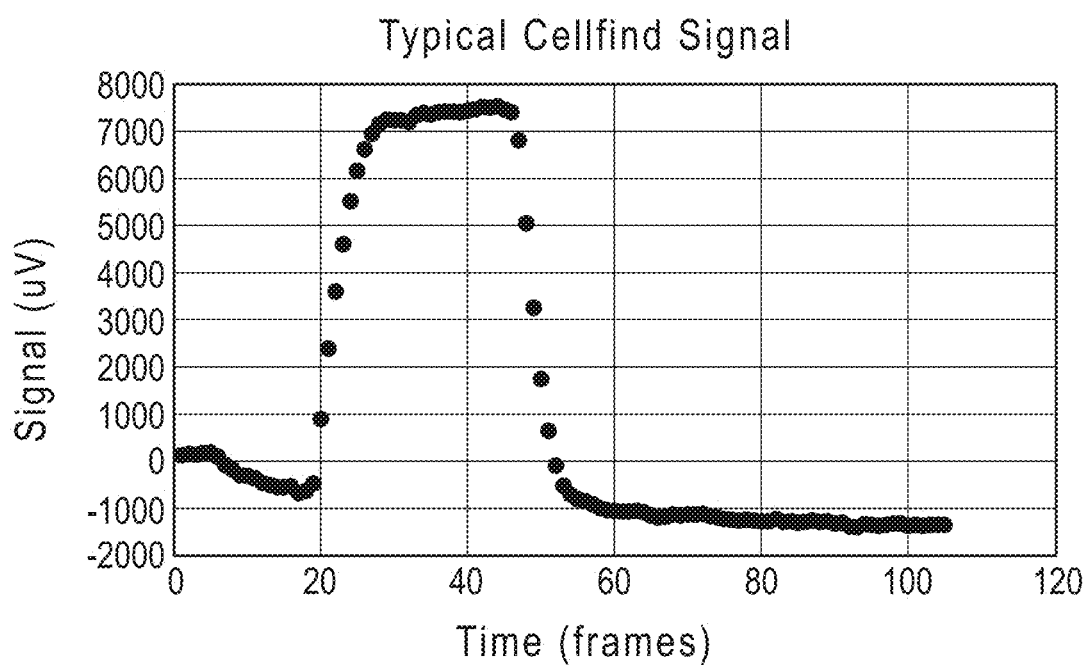
FIG. 6D is an example of a sensor signal corresponding to a single pixel in response to a CellFind flow.
Figure 6E:
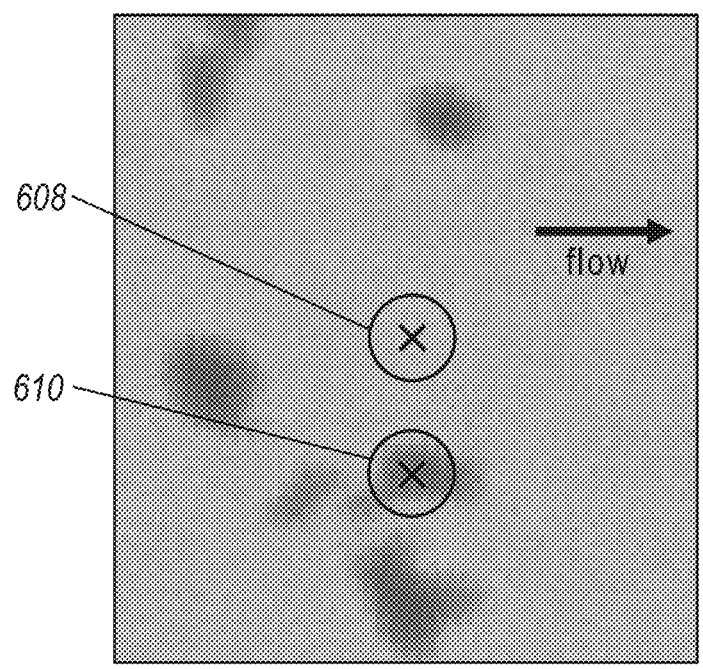
FIG. 6E shows an example of a tile having cell regions and background regions.
Figure 6F:
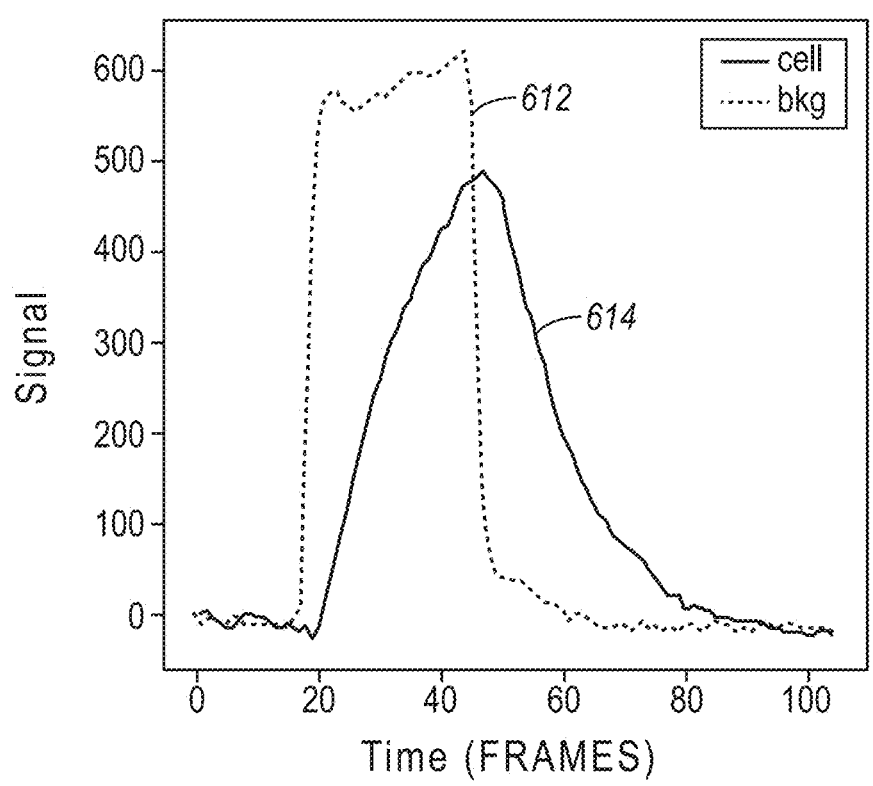
FIG. 6F show examples of plots of sensor signals corresponding to two pixels in the tile of FIG. 6E in response to a CellFind flow over time.

FIG. 6A shows an example of a grayscale image of a single frame of a tile's response to a CellFind flow. FIG. 6D shows an example of a plot of sensor signal corresponding to a single pixel in response to a CellFind flow over time. FIG. 6E shows an example of a tile having cell regions and background regions. The arrow in FIG. 6E denotes that reagents, such as for the CellFind flow, flow from left to right. FIG. 6F show examples of plots of sensor signals corresponding to two pixels in the tile of FIG. 6E in response to a CellFind flow over time. The sensor signal corresponding to a pixel in cell region 610 of FIG. 6E produced the plot 614 in FIG. 6F. The sensor signal corresponding to a pixel in background region 608 of FIG. 6E produced the plot 612 in FIG. 6F. The time axis for FIG. 6F is in units of frames (at 15 fps). In this example, the CellFind reagent flows for 2 seconds (from frame 15 to frame 45) which spans both the rising and falling sensor signals in response to the change in pH of the CellFind flow. The examples of FIGS. 6E and 6F show that regions of the sensor array covered with a cell have a slower response to the CellFind flow than background regions not covered by a cell.

The processor may apply the electroscopic image segmentation step 304 to the electroscopic image data to segment the 2D images into one or more cell regions corresponding to locations of cells on the sensor array and background regions corresponding to areas on the sensor array having no cells. The selection of cell signals and background signals step 306 may select signals corresponding to the locations of cell regions and background regions in the 2D images. In the following, the terms "image" and "tile" may be used interchangeably, as both are images. The signal parameterization step 308 may combine and parameterize signal samples corresponding to pixels in the cell regions. The user display and interaction step 310 may present selected signals and parameterizations to a user.

Figure 4A:
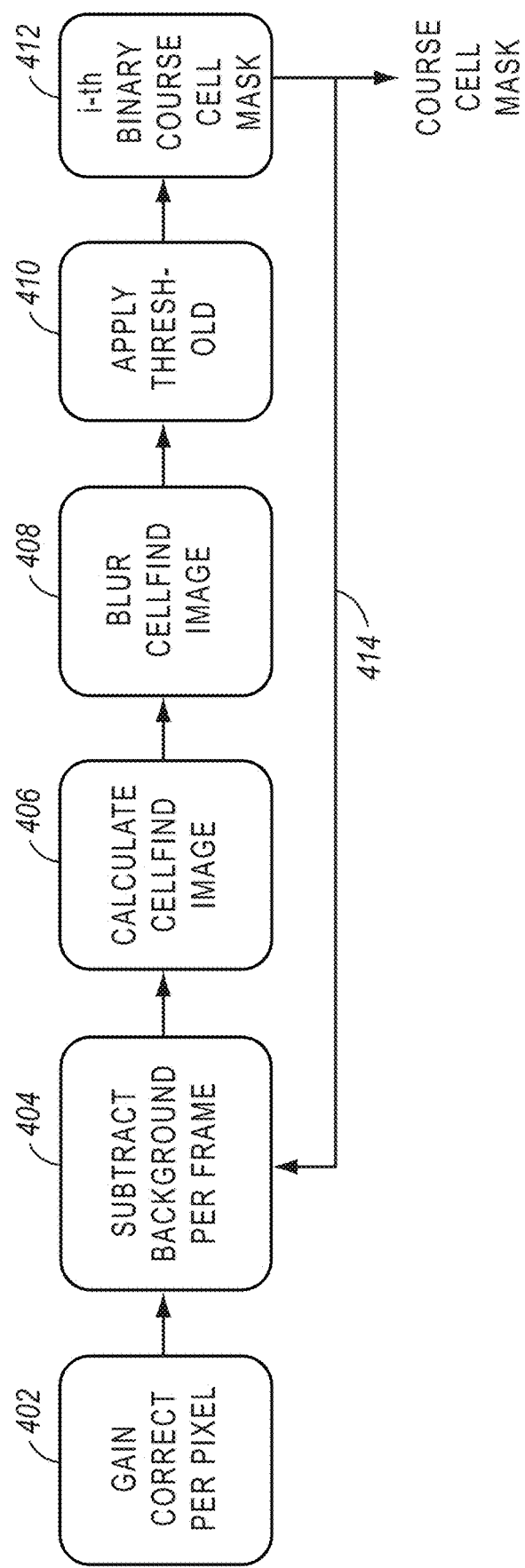
FIG. 4A is a block diagram of the electroscopic image segmentation 304, in accordance with an embodiment.

FIG. 4A is a block diagram of the electroscopic image segmentation 304, in accordance with an embodiment. In step 402, the gain may be corrected for each pixel in the frame. At the beginning of each experiment, the electrical gain of each pixel is determined by applying an external perturbation to the fluidic potential and comparing the measured step size per pixel to the expected step size. The gain for each pixel may be corrected by dividing the pixel value in the frame by the electrical gain for the pixel. In step 404, a background value for each pixel is subtracted from each pixel the frame. For example, a global background value per frame may be determined by calculating the statistical mode of all the pixel values in the frame. The global background value is calculated and subtracted from each pixel on a frame-by-frame basis for every frame acquired during the acquisition interval. In step 406, pixel values for a 2D CellFind image (CI) may be calculated over the acquisition time interval. The pixels of a CellFind image comprise values of features calculated based on characteristics of the signal samples measured in response to the CellFind flow. The pixels of the CellFind image may be thresholded to form a binary CellFind image, where pixel values greater than or equal to the threshold are assigned a value of 1, pixel values less than the threshold are assigned a value of 0. Pixel values of 1 in the CellFind image indicate a possible presence of a cell. The CellFind image may be determined on a tile by tile basis for each frame in the acquisition time interval. In some embodiments, a plurality of CellFind images may be calculated corresponding to the same tile, wherein each CellFind image measures specific characteristics, as described below.

In step 408, a blurring function may be applied to the CellFind image calculated. In some embodiments, the CellFind image may be blurred by applying a low-pass filter in the frequency domain as follows:

A. For each tile of the CellFind image, calculate a 2D Fourier Transformation, for example, a 2D Fast Fourier Transformation (FFT), to form a frequency domain image.

B. Apply a low-pass filter in the frequency domain to form a frequency domain filtered image. For example, a Butterworth filter may be applied. An exemplary Butterworth filter equation is given by $$\exp(-r^{2.5}/1.5N^3) \qquad (1)$$

where $r=X^2+Y^2$, where X and Y are coordinates in the frequency domain, and N is the minimum number of components in either X or Y.

C. Calculate the inverse 2D Fourier Transform, for example the inverse 2D FFT, of the frequency domain filtered image.

D. Keep the real part of the inverse 2D FFT to form pixel values of a blurred CellFind image.

In step 410, a threshold T may be applied to the pixel values of the blurred CellFind image to produce a binary image with 1's in pixel locations where the blurred CellFind image's pixel values are greater than or equal to T and 0's in pixel locations where the blurred CellFind images's pixel values are less than T. In some embodiments the threshold T may be calculated by the following equation:

$$T=(\text{mean}+[\text{max-algo\_min}]*\text{frac}) \qquad (2)$$

In equation (2), the mean and max may be determined for the pixel values of the blurred CellFind values of the tile. The fraction, "frac", may be defined by the user. For example, the frac value may be set to 0.1. The resulting binary CellFind image provides a coarse cell mask 412, where approximate locations of cells are indicated by the 1's and background regions are indicated by the 0's.

In some embodiments, the CellFind image may comprise a "peak-to-peak (PTP)" image determined for frames in the acquisition time interval. The PTP value for a pixel in the PTP image may be determined by the following steps:

a. Subtract the minimum pixel value from the maximum pixel value for each pixel location in the tile during the acquisition time interval.

b. Blur the PTP image (step 408).

c. Apply a threshold T to the pixel values of the blurred PTP image (step 410) according to equation (2). For example, the algo_min may be set to 100, which is 25% of the typical maximum PTP value. The algo_min may range from 10% to 100% of the maximum value of the PTP image.

d. Pixel values greater than or equal to the threshold are assigned a value of 1, pixel values less than the threshold are assigned a value of 0 to form a binary CellFind image (step 412).

In some embodiments, the CellFind image comprises an image of "peak-to-peak absolute values (PTP-Abs)" determined for frames in the acquisition time interval. The PTP-Abs image may be determined by the following steps:

a. Calculate the PTP image for the acquisition time interval.

b. Calculate the mean PTP value of the pixels in the PTP image.

c. Subtract the mean PTP value from the PTP value of each pixel in the PTP image to form a difference image.

d. Calculate the absolute value of the difference for each pixel in the difference image to form an absolute difference image.

e. Add the mean PTP value to each pixel to form the PTP-Abs image.

f. Blur the PTP-Abs image (step 408).

g. Apply a threshold T to the pixel values of blurred PTP-Abs image (step 410) according to equation (2). For example, the algo_min may be set to 100. The algo_min may range from 10% to 100% of the maximum value of the PTP-Abs image. The algo_min value of 100 is 25% of a typical maximum PTP-Abs value. Pixel values greater than or equal to the threshold are assigned a value of 1, pixel values less than the threshold are assigned a value of 0 to form a binary CellFind image (step 412).

In some embodiments, the CellFind image may comprise a "maximum variation (MaxVar)" image determined for frames in the acquisition time interval. A MaxVar image may be determined by the following steps:

a. Calculate the mean value of the pixels of the tile at each frame time, or sampling time, to give an array of mean values. For example, for 105 frames in an acquisition time interval, 105 mean values are calculated to give a 1×105 array of mean values corresponding to tile.

b. Calculate the differences between adjacent mean values in the array of mean values to form an array of difference values. For example, for the 1×105 array of mean values, an 1×104 array of difference values is calculated.

c. Identify the frame with the largest difference in the array of difference values as frame $f_{max}$.

d. Calculate the difference between the tile($f_{max}$) and the tile of first frame ($f_1$) in the acquisition time interval tile($f_1$). MaxVar image=tile($f_{max}$)−tile($f_1$).

e. Blur the MaxVar image (step 408).

f. Apply a threshold T to the pixel values of blurred MaxVar image (step 410) according to equation (2). For example, the algo_min may be set to 100. The algo_min may range from 10% to 100% of the maximum value of the MaxVar image. Pixel values greater than or equal to the threshold are assigned a value of 1, pixel values less than the threshold are assigned a value of 0 to form a binary CellFind image (step 412).

In some embodiments, the CellFind image may comprise a composite of MaxVar sub-images determined for sub-tiles of frames in the acquisition time interval, referred to herein as "MaxVar local" images. A MaxVar local image may be determined by the following steps:

a. Divide the tile into a plurality of sub-tiles. The sub-tile dimensions may be 5% to 50% of the full tile dimensions. For example, for tile dimensions of 664×640, the sub-tile dimension may be approximately 80×80.

b. Calculate a MaxVar local image for each sub-tile, independent from the other sub-tiles. An array of mean values and array of difference values are calculated for each sub-tile. A frame $f_{max}$ and sub-tile($f_{max}$) is identified for each sub-tile. Each MaxVar local image will correspond to MaxVar local image=sub-tile($f_{max}$)−sub-tile($f_1$)

c. Generate a composite MaxVar local image from the MaxVar local images determined for the sub-tiles.

d. Blur the composite MaxVar local image (step 408).

e. Apply a threshold T to the pixel values of the blurred composite MaxVar local image (step 410) according to equation (2). For example, the algo_min may be set to 100. The algo_min may range from 10% to 100% of the maximum value of the composite MaxVar local image.

f. Pixel values greater than or equal to the threshold are assigned a value of 1, pixel values less than the threshold are assigned a value of 0 to form a binary CellFind image (step 412).

In some embodiments, the CellFind image may comprise a function of temporal averages of the pixels of the tiles over the acquisition time interval to form a temporal average image. The temporal average image may be determined by the following steps:

a. Calculate an average over the acquisition time interval of each pixel value in the tile to form a first average image.

b. Calculate an average over a plurality of initial frames in the acquisition time interval of each pixel value in the tile to form a second average image. The number of frames in the plurality of initial frames can range from 5% to 50% of the total number of frames in the acquisition time interval. For example, the number of initial frames may be the first 10 frames and the total number of frames may be 105 frames in the acquisition time interval.

c. Subtract the second average image from the first average image to form a temporal average image.

d. Blur the temporal average image (step 408).

e. Apply a threshold T to the pixel values of blurred temporal average image (step 410) according to equation (2). For example, the algo_min may be set to 100. The algo_min may range from 10% to 100% of the maximum value of the temporal average image.

f. Pixel values greater than or equal to the threshold are assigned a value of 1, pixel values less than the threshold are assigned a value of 0 to form a binary CellFind image (step 412).

In some embodiments, the CellFind image may comprise a "time-to-peak (tPeak)" image. The tPeak image may be determined by the following steps:

a. For each pixel location, determine the maximum pixel value during the acquisition time interval.

b. For each maximum pixel value, determine the frame index, or number of frames, corresponding to the maximum pixel value.

c. Form the tPeak image where each pixel location has the frame index, or number of frames, corresponding to the maximum pixel value.

d. Blur the tPeak image (step 408).

d. Apply a threshold T to the pixel values of blurred tPeak image (step 410) according to equation (2). For example, algo_min may be set to 4 frames. The algo_min may range from 1 to the total number of frames in the acquisition time interval.

e. Pixel values greater than or equal to the threshold are assigned a value of 1, pixel values less than the threshold are assigned a value of 0 to form a binary CellFind image (step 412).

In some embodiments, the CellFind image may comprise a "time-to-peak 80% (tPeak80)" image. The tPeak80 image may be determined by the following steps:

a. For each pixel location, determine the maximum pixel value during the acquisition time interval.

b. Calculate 80% of the maximum pixel value for each pixel location c. Determine the frame index, or number of frames, corresponding to the 80% maximum pixel value.

d. Form the tPeak80 image where each pixel location has the frame index, or number of frames, corresponding to the maximum pixel value.

e. Blur the tPeak80 image (step 408).

f. Apply a threshold T to the pixel values of blurred tPeak80 image (step 410) according to equation (2). For example, the algo_min may be set to 3 frames. The algo_min may range from 1 to the total number of frames in the acquisition time interval.

g. Pixel values greater than or equal to the threshold are assigned a value of 1, pixel values less than the threshold are assigned a value of 0 to form a binary CellFind image (step 412).

In some embodiments, the CellFind image may comprise a "time-to-peak local (tPeak local)" image. The tPeak local image may be determined by the following steps:

a. For each pixel location, determine the maximum pixel value during the acquisition time interval.

b. For each maximum pixel value, determine the frame index, or number of frames, corresponding to the maximum pixel value to produce a tPeak image c. Divide the tPeak image into sub-tiles. The sub-tile dimensions may be 5% to 50% of the full tile dimensions. For example, for tile dimensions of 664×640, the sub-tile dimension may be approximately 80×80.

d. For each sub-tile, subtract the average pixel value within the sub-tile.

e. Generate a composite tPeak local image comprising the sub-tiles.

h. Blur the composite tPeak local image (step 408).

i. Apply a threshold to the pixel values of the blurred tPeak local image (step 410) according to equation (2). For example, the algo_min may be set to 7 frames. The algo_min may range from 1 to the total number of frames in the acquisition time interval.

j. Pixel values greater than or equal to the threshold are assigned a value of 1, pixel values less than the threshold are assigned a value of 0 to form a binary CellFind image (step 412).

In some embodiments, the CellFind image may comprise a "time-to-fall (tFall local)" image. This is an indicator of the return to the original pH on the falling side of the signal. The tFall local image may be determined by the following steps:

a. Divide the tile into sub-tiles. The sub-tile dimensions may be 5% to 50% of the full tile dimensions. For example, for tile dimensions of 664×640, the sub-tile dimension may be approximately 80×80.

b. Calculate the mean value of the pixels of the sub-tile at each frame time, or sampling time, to give an array of mean values. For example, for 105 frames in an acquisition time interval, 105 mean values are calculated to give a 1×105 array of mean values corresponding to sub-tile.

c. Find the frame index $f_{max}$, or time index, corresponding to the maximum mean value in the array of mean values corresponding to the sub-tile.
d. Identify the sub-tile corresponding to the frame index, sub-tile($f_{max}$).
e. For the corresponding sub-tile in the last frame fiast, sub-tile(fiast), calculate the difference image=sub-tile($f_{max}$)−sub-tile(fiast).
f. Calculate a fraction of each pixel value the difference image to give a fractional value. For example, the fractional value may be 25%. A range of values for the fractional value is 5% to 90%.
g. Add the fractional value to the pixel value in the sub-tile(fast) to form a threshold image for the sub-tile.
h. For each pixel location in the sub-tile, determine the frame index $f_T$, or number of frames, when the pixel value falls below the threshold corresponding to the pixel location in the threshold image.
i. For each pixel location in the sub-tile, subtract $f_{max}$ from $f_T$ to form a tFall local image corresponding to the sub-tile.
j. Combine tFall local images corresponding to the sub-tiles to form a composite tFall image corresponding to the tile.
k. Blur the composite tFall image (step 408).
l. Apply a threshold to the pixel values of the blurred composite tFall image (step 410) according to equation (2). For example, the algo_min may be set to 6 frames. The algo_min may range from 1 to the total number of frames in the acquisition time interval.
m. Pixel values greater than or equal to the threshold are assigned a value of 1, pixel values less than the threshold are assigned a value of 0 to form a binary CellFind image (step 412).

In some embodiments, a Pearson Difference (PD) may be calculated from the binary CellFind image derived from any of the CellFind methods described above. The estimated binary mask divides the pixels into initial estimates of "cell" regions and "background" regions. A Pearson Difference may be calculated for each pixel of the estimated CellFind image as follows, $$PD = P_{o,c} - P_{o,b} \quad (3)$$

where $P_{o,c}$ is the Pearson correlation between the time series for an object and the average time series of all pixels identified as cells in the binary mask and $P_{o,b}$ is the Pearson correlation between the time series of an object and the average time series of all pixels identified as background. In this instance, an object is an individual pixel. The Pearson correlation may be calculated as follows:

$$P_{x,y} = \text{cov}(x,y)[\text{std}(x)*\text{std}(y)] \quad (4)$$

where $P_{x,y}$ is the Pearson correlation coefficient for time series x and time series y, cov(x,y) is the covariance of time series x and time series y, std(x) is the standard deviation of time series x and std(y) is the standard deviation of time series y. The time series for the average of all pixels in regions defined as cells is calculated (typically 1×105, for 105 frames in the acquisition time interval). The time series for the average of all pixels in regions defined as background is calculated (typically 1×105, for 105 frames in the acquisition time interval). The time series for the object is calculated. In this instance, an object can be a single pixel or an average of one or more pixels (typically 1×105, for 105 frames in the acquisition time interval). The Pearson Difference (PD) CellFind image calculated by equation (3) may be divided into cell regions and background regions using Otsu's method (www.en.wikipedia.org/wiki/Otsu%27s_method). A histogram of the PD CellFind image may be calculated. The histogram may have two peaks corresponding to two classes, one for the cell regions and one for the background regions. Otsu's method determines a single threshold value that would optimally separate the pixels into two classes corresponding to the two peaks in the histogram of the PD CellFind image by minimizing the intra-class variance. The threshold value may be applied to the PD CellFind image to produce a binary PD CellFind image.

The $i^{th}$ coarse cell mask from step 412 may be provided in an (i+1) iteration 414 for calculation of local background values in step 404. The local background value may be determined by applying a convolutional kernel to the pixel values of the tile. In some embodiments, the convolutional kernel may be a rectangular array of coefficients. For example, the convolutional kernel may have a center coefficient of 0 and all other coefficients equal to 1. Convolving the kernel with the pixel values of the tile and dividing by the number of 1's in the kernel generates a local spatial average for the background value at the pixel location corresponding to the center coefficient. FIG. 5 gives an example (not to scale) of a convolutional kernel that could be used to calculate a local spatial average of pixel values. The dimensions of the convolutional kernel may be configurable by the user. For example, for tile dimensions of 640 by 664 pixels, the convolutional kernel may have dimensions of 41 pixels in a horizontal dimension by 101 pixels in a vertical dimension. The horizontal dimension parallels the direction of the CellFind flow. The vertical dimension is perpendicular to the direction of the CellFind flow. The CellFind flow proceeds from one side of the sensor array to the other. FIG. 6E shows an example of the direction of the CellFind flow across a tile from left to right. In some embodiments, the number of pixels in the convolutional kernel may be 6% of the number of pixels in the tile. In some embodiments, the number of pixels in the convolutional kernel may range from 3% to 20% of the number of pixels in the tile. In some embodiments, the pixel locations corresponding to a coarse cell mask value of 1 are excluded from the convolution input and a local background may be estimated in the absence of the cells identified in the coarse cell mask. The array of local background values may be subtracted from the pixel values of the tile at corresponding pixel locations to form a local background corrected tile. An array of local background values may be determined for all the tiles in each frame and subtracted from each frame of the acquisition time interval using the same coarse cell mask to produce corresponding local background corrected frames.

In an (i+1) iteration for step 406, a CellFind image value for each pixel in the local background corrected frames is calculated to form a local background corrected CellFind image, as described above.

In an (i+1) iteration for step 408, the blurring function may be applied to the local background corrected CellFind image. In an (i+1) iteration for step 410, a threshold may be applied to the pixel values of the blurred local background corrected CellFind image to produce a binary image with 1's in pixel locations where the blurred local background corrected CellFind values are greater than or equal to $T_{i+1}$ and 0's in pixel locations where the blurred local background corrected CellFind values are less than $T_{i+1}$. In some embodiments the threshold $T_{i+1}$ may be calculated by equation (5), $$T_{i+1} = (\text{mean}_{i+1} + [\text{max}_{i+1} - \text{algo\_min}]*\text{frac}_{i+1}) \quad (5)$$

In equation (5), the mean$_{i+1}$ and max$_{i+1}$ may be determined for the pixel values of the blurred local background corrected CellFind values of the tile. The fraction, "frac$_{i+1}$", may be defined by the user. For example, the frac$_{i+1}$ value may be set to 0.1. The range of the frac$_{i+1}$ value is 0<frac$_{i+1}$<frac. The resulting binary image provides a local background corrected cell mask, where approximate locations of cells are indicated by the 1's and background regions are indicated by the 0's. In some embodiments, the local background corrected cell mask may be determined for the acquisition time interval.

FIG. 6A shows an example of a grayscale image of a tile's response to a CellFind flow. FIG. 6B shows an example of a tile of a coarse cell mask. FIG. 6B represents the first interation (i=1) coarse cell mask 412 before local background correction. FIG. 6C shows an example of a tile of a local background corrected cell mask after two iterations (i+1=2). FIG. 6C represents the local background corrected cell mask after local background subtraction of step 404, the CellFind calculation of step 406 using the peak-to-peak (PTP) calculation described above, the blurring operations of step 408 and the thresholding of step 410. The features represent approximate possible cell locations. Features in the local background corrected cell mask of FIG. 6C are more numerous and enhanced than those in the coarse cell mask of FIG. 6B. For example, the cluster of features 602 in FIG. 6B and the cluster of larger features 604 in FIG. 6C correspond to the cluster of features 601 in the grayscale image of the tile's response.

Figure 4B:
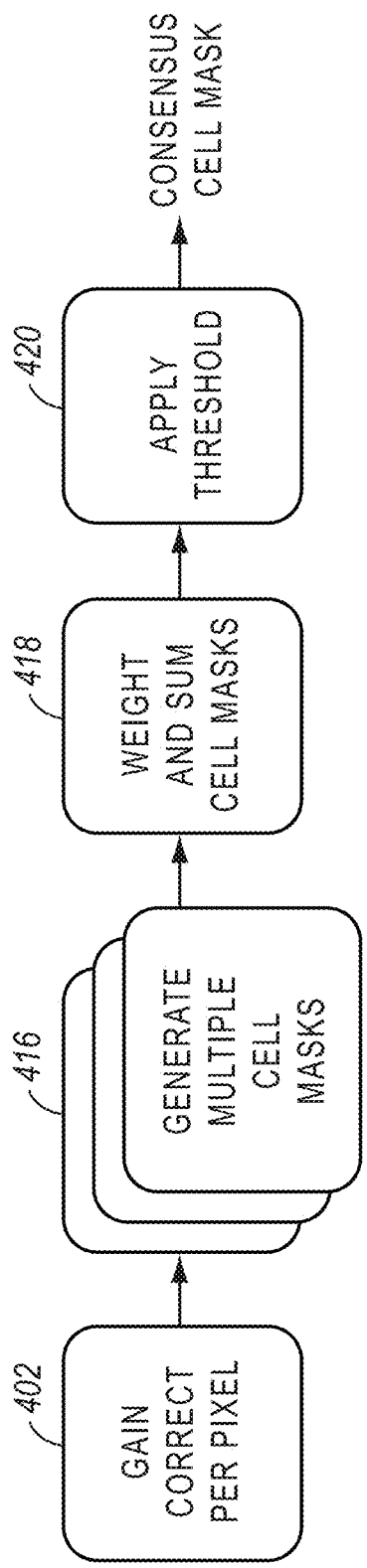
FIG. 4B is a block diagram for forming a consensus cell mask, in accordance with an embodiment.

In some embodiments, multiple cell masks may be generated by calculating more than one of the types of the CellFind images described above. FIG. 4B is a block diagram for forming a consensus cell mask, in accordance with an embodiment. In step 416, a plurality of different types of CellFind images may be calculated as described above with respect to FIG. 4A steps 404 to 412, to produce a plurality of cell masks. In step 418, the cell masks may be weighted and summed as follows:

$$\text{Weighted Sum Image} = \Sigma_j w_j \times \text{cell mask}_j \quad (6)$$

A conversion from a binary data type in the cell mask$_j$ to a floating point data type may be applied before the multiplication by the weights $w_j$. In step 420, a first threshold may be applied to the weighted sum image. Pixel values greater than or equal to the first threshold are assigned a value of 1, pixel values less than the threshold are assigned a value of 0 to form a binary consensus cell mask. For example, the first threshold applied to the weighted sum image may be set to a relatively large value of 1.8 in order to identify regions highly likely to be cells. In some embodiments, a second consensus cell mask may be generated by applying a second threshold to the weighted sum image in step 420. For example, the second threshold may have a lower value than the first threshold, such as 0.7. Since the second threshold is lower, the second consensus cell mask allows more possible cell regions while allowing for some degree of error. The range of values for the first threshold and second threshold is from min($w_j$) to $\Sigma_j w_j$. For example, the first threshold is selected to have a low false positive rate for identifying cells. The second threshold is selected to have a low false negative rate for identifying cells.

Table A gives exemplary values for the weights $w_j$. When a particular CellFind image type will not be used, the corresponding weight $w_j$ may be set to zero. Values of the weights $w_j$ may be selected by the user.

| $j^{th}$ CellFind Image Type | Example Weight $w_j$ | Example Range of Weights $w_j$ |
|---|---|---|
| Peak to Peak (PTP) | 1.0 | 0-1 |
| Peak to Peak Absolute Value (PTP-Abs) | 1.0 | 0-1 |
| Max Var | 0.8 | 0-1 |
| MaxVar Local | 0.8 | 0-1 |
| Mean | 1.0 | 0-1 |
| tPeak | 0.8 | 0-1 |
| tPeak 80 | 0.8 | 0-1 |
| tPeak Local | 0.1 | 0-1 |
| tFall Local | 0.5 | 0-1 |
| Pearson Difference (PD) | 1.0 | 0-1 |

Figure 4C:
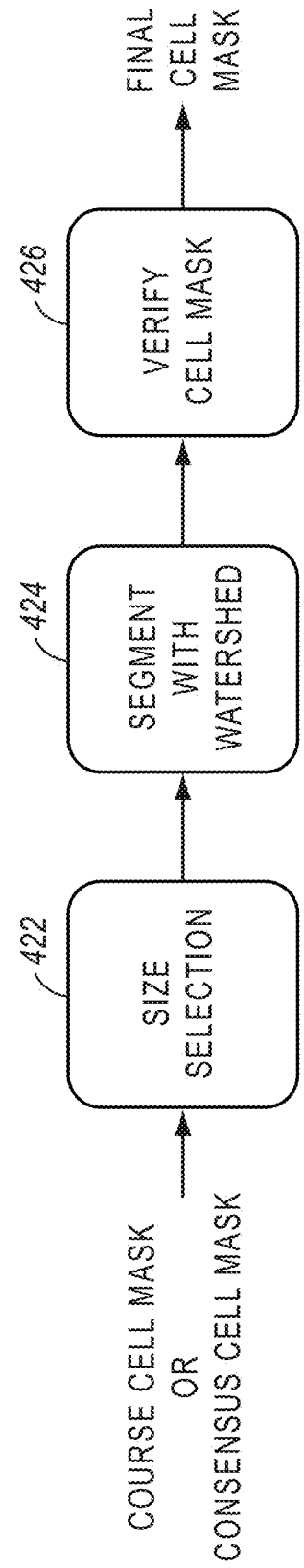
FIG. 4C is an exemplary block diagram for forming a final consensus cell mask.

FIG. 4C is an exemplary block diagram for forming a final consensus cell mask. In embodiments where only one type of CellFind image is calculated as described above with respect to FIG. 4A, the coarse cell mask is the input cell mask to the size selection step 422. In embodiments where multiple types of CellFind images are calculated as described above with respect to FIG. 4B, the consensus cell mask is the input cell mask to the size selection step 422. For the size selection step 422, the sizes of features in the input cell mask corresponding to sizes of interest are detected. For example, sizes of interest for analysis of cells may be in the range of 20-75 microns. The sizes of interest may correspond to effective diameters, der, where, $$d_{\textit{eff}} = \sqrt{\frac{4}{\pi} A_{px} p_{area}} \quad (7)$$

where $A_{px}$ is the area of the cell, in pixels, and $p_{area}$ is the area per pixel. The sizes of interest may correspond to areas in a range 314-4400 square microns. An area of a pixel of the ChemFET sensor array may be known based on the dimensions of the sensors. A size of interest for a feature may be converted to a corresponding number of pixels or an effective area in pixels. The input cell mask is segmented and continuous regions of a feature may be identified and labeled. The continuous regions of a feature may be filtered based on whether the feature's area in pixels falls within the range of areas of interest. The selected features are retained in a filtered cell mask and have pixel values of 1. The features that do not have areas with the range of areas of interest may be assigned pixel values of 0 in the filtered cell mask, defining them as background regions. The range of thresholds in pixels for features may be greater than 8.

In step 424, the filtered cell mask is segmented using a watershed algorithm. The watershed algorithm segments a selected feature into one or more cell regions. In the filtered cell mask, each selected feature has pixel values of 1 and the background regions have pixel values of 0. The filtered cell mask is segmented as follows:

a. For pixels of filtered feature regions in the filtered cell mask (i.e., pixels having a pixel value of 1), calculate the distance to the nearest background pixel (i.e., pixel having a pixel value of 0).
 b. Identify one or more local maxima of the calculated distances in a given filtered feature region. Each local maximum corresponds to a centroid.
 c. Classify each pixel in the filtered feature region based on its distance(s) to the one or more centroids of the filtered feature region. Assign each pixel in the filtered feature region to the nearest centroid. A group of pixels assigned to the same centroid are classified as a cell region.

d. Create a labeled mask image by assigning an index to pixel locations in each cell region determined in step c. For example, a first cell region may have 1's assigned to its pixel locations, a second cell region may have 2's assigned to its pixel locations, etc.

In step 426, the cell mask may be verified to produce a final cell mask. The cell mask resulting from segmentation step 424 may indicate an excess of cell regions. Some of the identified cell regions may be errors and really correspond to a background region. In step 426, the cell mask produced by step 424 may be divided spatially into multiple sub-regions. The CellFind images acquired during the acquisition time interval may be divided spatially into corresponding multiple sub-regions. For example, the cell mask and the Cell-Find images may each be divided into 4 quadrants. The range of sub-regions may be 1-100 sub-regions. For each cell region, the Pearson Difference (equation 3) may be calculated between the cell average time series and the cell and background time series for the nearest sub-region. In this instance, an "object" corresponds to a particular cell and the variable "o" in $P_{o,c}$ or $P_{o,b}$ is the average time series of the pixels defined as belonging to a single particular cell. The variable "c" in $P_{o,c}$ is the average time series of all pixels defined as belonging to any cell, according to the first threshold applied to the weighted sum image in step 420. The variable "b" in $P_{o,b}$ is the average time series of all pixels defined as belonging to the background, according to the second threshold applied to the weighted sum image in step 420. The resultant PD values per cell are stored in a 1×N array, where N is the total number of cells identified in the cell mask. In some embodiments, in order to add numerical stability, one or more "fake cells" may be generated by randomly selecting pixels from the background region. The size of the fake cell can range from 10 pixels to 100% of the background region. A typical size is 20% of the background region. The number of fake cells can range from 5% of the identified cell regions to 100% of the identified cell regions in the cell mask. A typical number is 10% of the identified cell regions. For each fake cell, the Pearson Difference may be calculated and appended to the values from the real cells to produce a 1×(N+F) array, where F is the total number of fake cells added. The array of Pearson Differences may be partitioned into two clusters, for example, according to k-means clustering (www.scikit-learn.org/stable/modules/generated/sklearn.cluster.KMeans.html). The cluster with a larger average Pearson Difference is determined to comprise "real" cell regions, and the cluster with the smaller average value is determined to comprise segmentation artifacts. If more than 30% of the "fake cells" are found in the "real cell" cluster, then the real cell cluster is determined to comprise segmentation artifacts and no verified cells are associated with that cluster.

Using the final binary cell mask, a set of pixels near the centroid of each of the cell regions may be selected for analysis of signal data acquired during the acquisition time period. The selected subset of pixels near the centroid is referred to herein as the cell region of interest (ROI). The cell ROI may be selected by selecting a plurality of pixels surrounding the centroid and contained within the segmented region for that cell. The number of pixels selected may be defined by the user. For example, the number of pixels may be 25. A range for the number of pixels selected may be 1 pixel to number of pixels in the full area of the cell with labels corresponding to the labeled mask image.

A local background region for each cell region may be identified. The local background region for each cell region assigned background labels in the labeled mask image generated in the above step d. The signal data acquired for the background region during the acquisition time period may be used to remove offsets from the signal data of the cell ROI. The local background region for each cell region in the binary cell mask may be determined as follows.

An outer boundary for the local background region for a given cell region may be determined. For the cell region of a given cell, perform a first plurality of iterations of binary dilations of the cell region. The first number of iterations may be selected by the user. For example, the number of iterations may be 25. A range for the first number of iterations may be 15-150 iterations. The resulting regions defines an outer boundary of the local background surrounding the cell region. The first plurality of iterations of binary dilations produces a first binary mask with 1's inside the outer boundary and 0's outside the outer boundary.

An inner boundary for the local background region for a given cell region may be determined. For the cell region of a given cell, perform a second plurality of iterations of binary dilations. The second number of iterations is less than the number of iterations used to define the outer boundary and may be selected by the user. For example, the number of iterations may be 10. A range for the number of iterations may be 5-50 iterations. The resulting regions defines an inner boundary of the local background surrounding the cell region. The second plurality of iterations of binary dilations produces a second binary mask with 1's inside the inner boundary and 0's outside the inner boundary.

Calculating a binary difference between the second binary mask and the first binary mask may give a local background binary mask partially or fully surrounding the given cell region. The local background binary mask will contain 1's the region between the inner boundary and the outer boundary. The pixels of the local background binary mask may be annotated in the labeled mask image.

Any pixel defined as local background for a given cell region is located at a minimum distance from any cell region in the cell mask. The minimum distance may be set by the user. For example, the minimum distance may be 25 pixels. A given cell region may not be defined as a background for any other cell region. The inner boundary of the local background for a given cell region is spatially separated from the boundary of the cell region so that the cell region and local background are not adjacent to each other.

Figure 7:
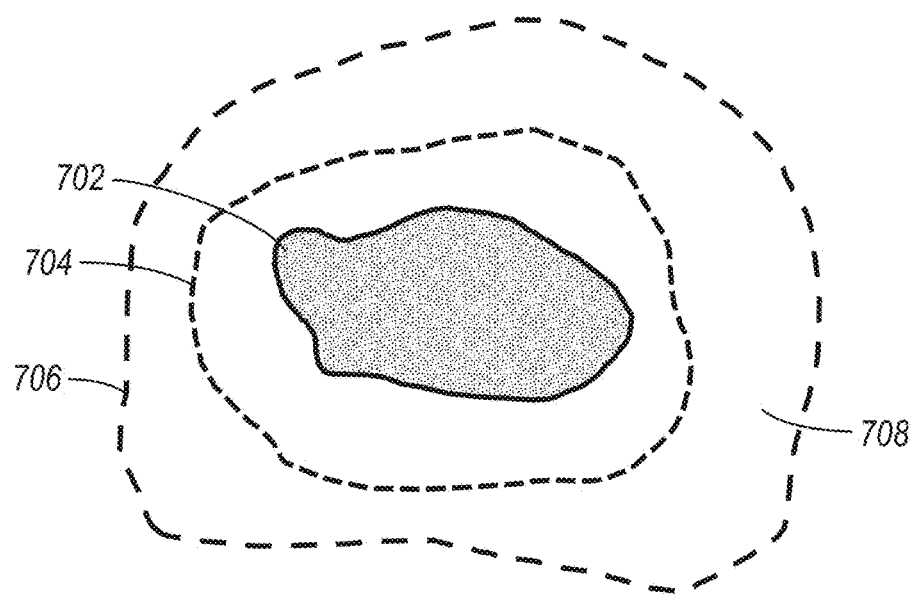
FIG. 7 is an illustration of an example of a single cell region and a local background region.

FIG. 7 is an illustration of an example of a single cell region and a local background region. The cell region 702 may be represented by pixel values of 1 in the cell mask. The outer boundary 706 may be determined by the first binary dilation. The inner boundary 704 may be determined by the second binary dilation. In this example, the local background region 708 surrounds the cell region 702 and is spatially separated from the boundary of the cell region 702. FIG. 7 is for illustrative purposes only and is not to scale.

Figure 8:
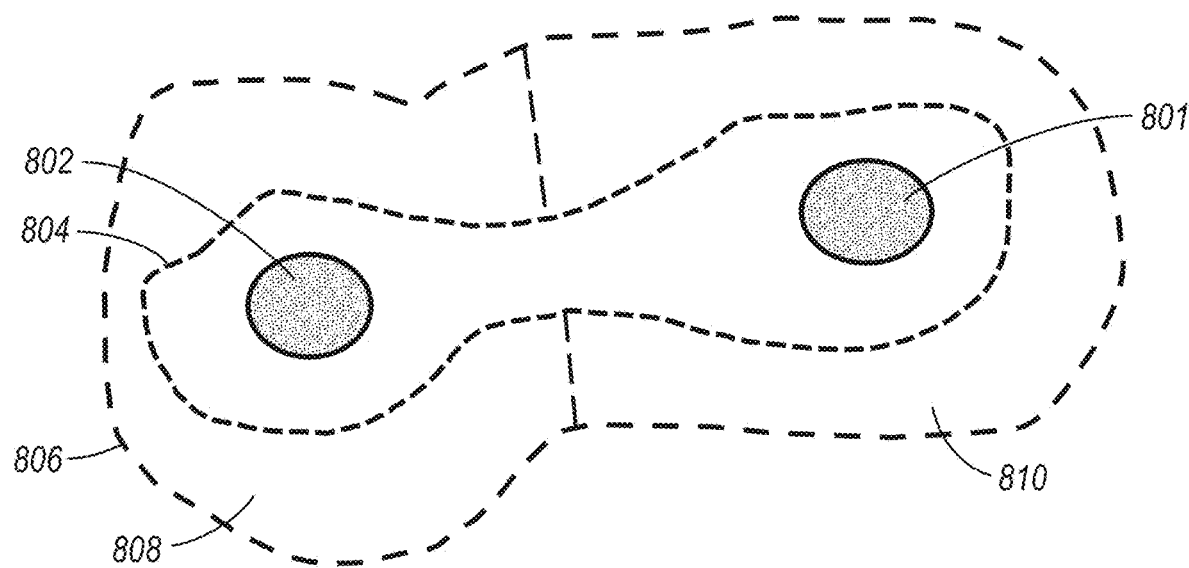
FIG. 8 is an illustration of an example of two cell regions and two local background regions.

FIG. 8 is an illustration of an example of two cell regions and two local background regions. The cell regions 801 and 802 may be represented by pixel values of 1 in the cell mask. The outer boundary 806 may be determined by the first binary dilation. The inner boundary 804 may be determined by the second binary dilation. In this example, the local background region 810 partially surrounds the cell region 801 and the local background region 808 partially surrounds the cell region 802. The local background regions 808 and 810 are spatially separated from the boundaries of the cell regions 801 and 802. FIG. 8 is for illustrative purposes only and is not to scale.

In some embodiments, a second consensus cell mask may be generated by using a lower threshold in step 420, as described above with respect to FIG. 4B. The inverse of the second consensus cell mask may be calculated. A binary dilation may be applied to the inverse of the second consensus cell mask. The resulting inverse mask may AND'ed with the local background binary mask to form a second local background binary mask.

Figure 9:
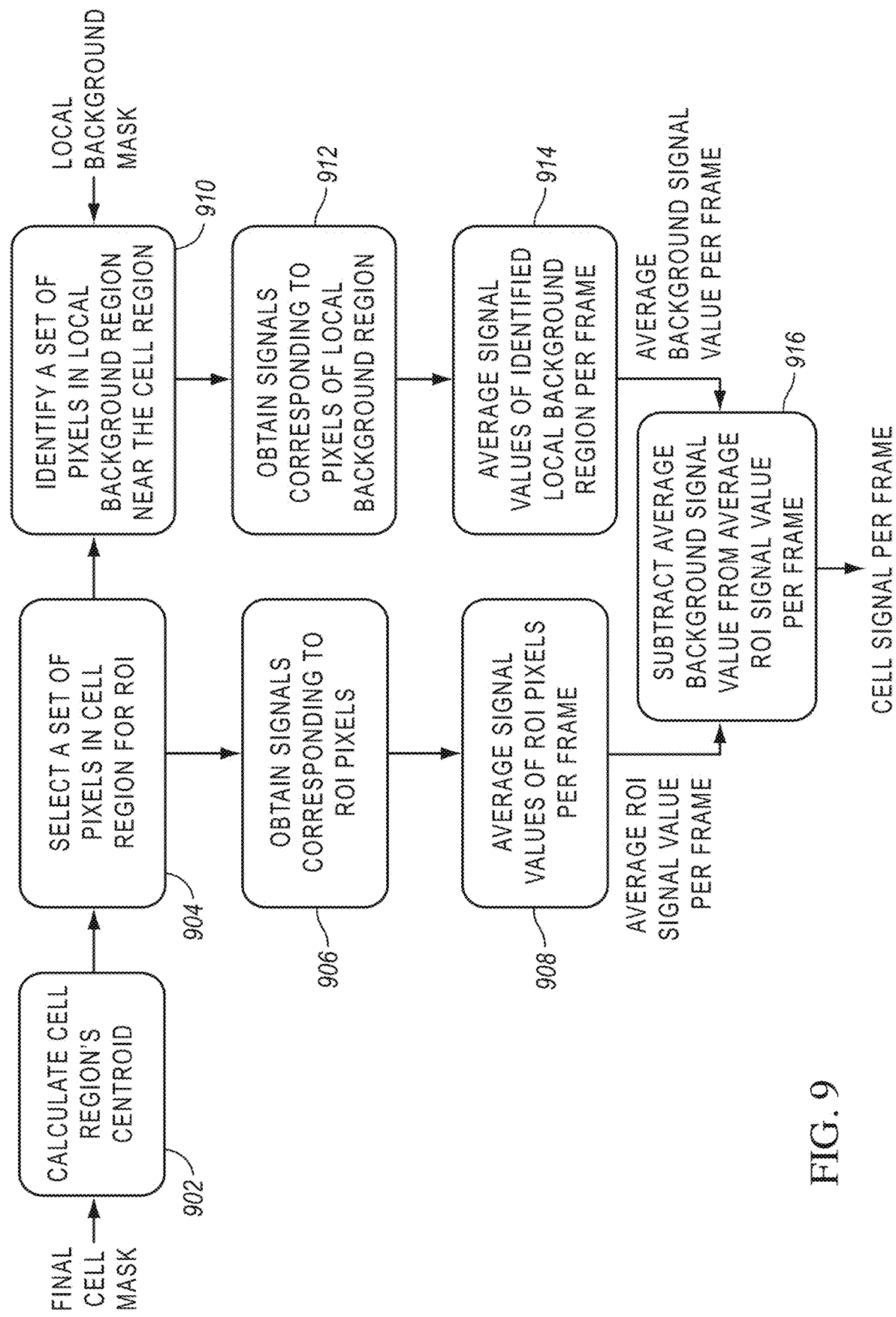
FIG. 9 is an exemplary block diagram for extracting signal data from cell regions of interest.
Figure 10:
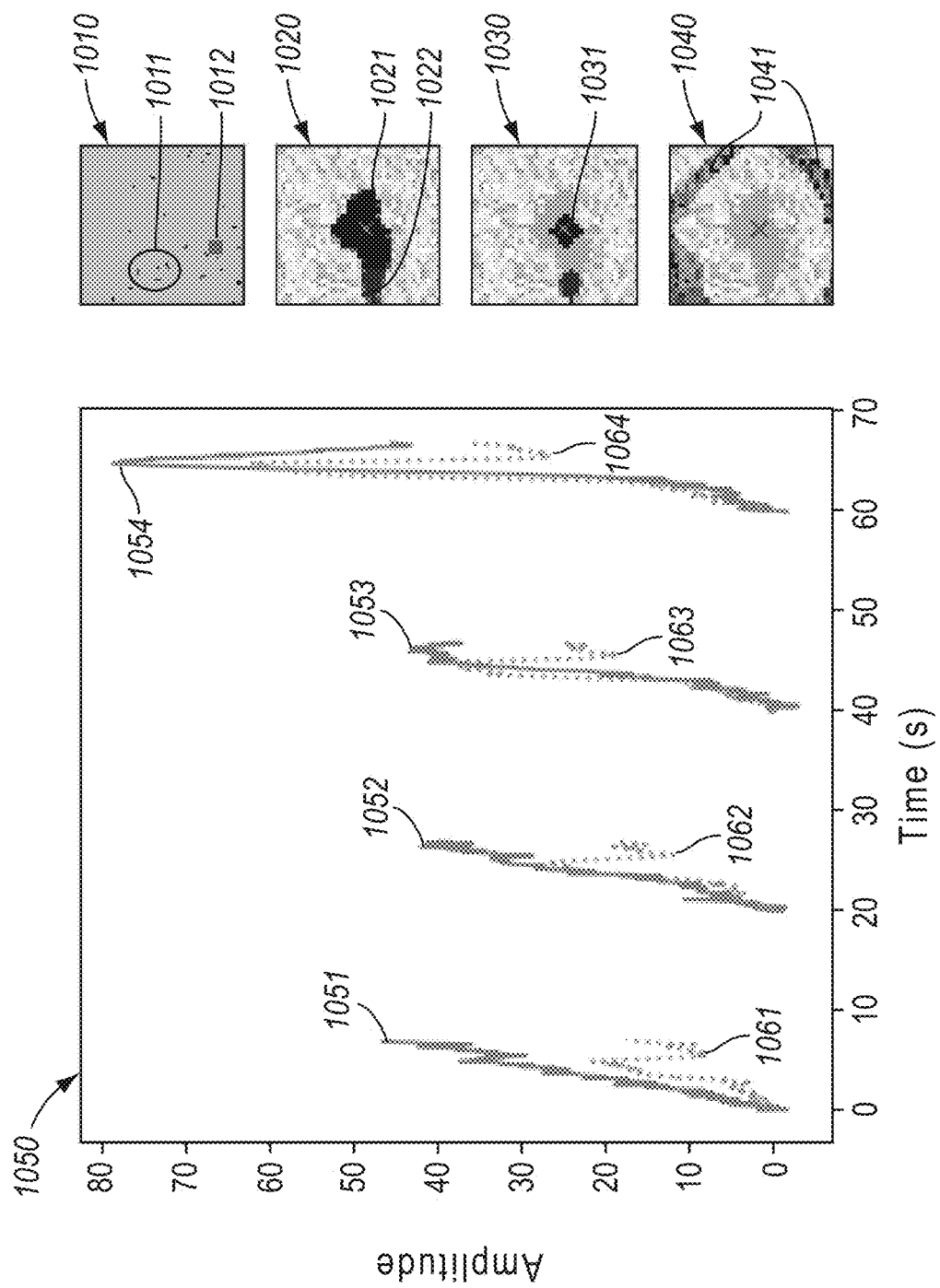
FIG. 10 gives examples of tile images, segmentation results and extracted signal data.

FIG. 9 is an exemplary block diagram for extracting signal data from cell regions of interest. FIG. 10 gives examples of tile images, segmentation results and extracted signal data. Image 1010 shows a final binary mask for a particular tile. Several cell regions are indicated, such as in the area 1011. In this example, area 1012 is selected for analysis of signal data. Image 1020 is a magnified view of area 1012 of the final cell mask 1010. Two cell regions are indicated, a set of pixels of cell region 1021 and a set of pixels of cell region 1022. This example focuses on cell region 1021. In step 902, the centroid of the set of pixels for cell region 1021 may be calculated. Calculation of the centroid may exclude the pixels of the boundary of the cell region 1021. The centroid is marked by "X" in images 1020, 1030 and 1040. In step 904, a subset of pixels within the cell region 1021 may be selected to define pixels of region of interest (ROI) 1031. For example, the subset of pixels selected for the ROI may surround the centroid. The number of pixels selected for the ROI 1031 may be selected by the user. For example, the number selected may be 25 pixels. In another example, a subset of pixels within the cell region 1021 may be selected by the user for an ROI.

In step 906, signals corresponding to the ROI pixels may be obtained. A signal corresponding to an ROI pixel comprises the sensor signal for the sensor at the corresponding location the ChemFET sensor array. The signal may be measured by the sensor after a reagent is flowed on the sensor array. The signals measured by sensors corresponding to the location of a cell may indicate the cell's response to the reagent. For each pixel, there is one signal sample per frame during the acquisition time interval. In step 908, the values of the signal samples may be averaged spatially for the pixels in the ROI at each frame time, or sampling time, to give an average signal value per frame. The number of pixels in the ROI determines the number of signal samples that are spatially averaged at each frame time, $t_{FRAME}$. The spatial average may be calculated as follows:

$$\text{Avg\_ROI\_sig}(t_{FRAME}) = \Sigma_{ROI} \text{sig}(t_{FRAME}, x_{ROI}, y_{ROI}) / N_{ROI} \quad (8)$$

where $\text{Avg\_ROI\_sig}(t_{FRAME})$ is the average ROI signal value per frame at time $(t_{FRAME})$, $\Sigma_{ROI}$ is the sum over pixels in the ROI (for example, ROI 1031), $\text{sig}(t_{FRAME}, x_{ROI}, y_{ROI})$ is the value of the signal sample at time $(t_{FRAME})$ at pixel coordinates $(x_{ROI}, y_{ROI})$ located in the ROI, and $N_{ROI}$ is the number of pixels in the ROI.

In step 910, a set of pixels in the local background region for the particular cell region may be identified in the local background mask. For example, image 1040 shows the local background region 1041 for the cell region 1021. In step 912, signals corresponding to the background pixels may be obtained. A signal corresponding to the background pixel comprises the sensor signal for the sensor at the corresponding location the ChemFET sensor array where no cell is present. The signal measured by the sensor after a reagent is flowed on the sensor array may represent effect of the flowed reagents on the sensor. In step 914, the values of the signal samples may be averaged spatially for the pixels in the background region at each frame time, or sampling time, to give an average signal value per frame. The number of pixels in the background region determines the number of signal samples that are spatially averaged at each frame time, $t_{FRAME}$. The spatial average may be calculated as follows:

$$\text{Avg\_bkg\_sig}(t_{FRAME}) = \Sigma_{BKG} \text{bkg\_sig}(t_{FRAME}, x_{BKG}, y_{BKG}) / N_{BKG} \quad (9)$$

where $\text{Avg\_bkg\_sig}(t_{FRAME})$ is the average background signal value per frame at time $(t_{FRAME})$, $\Sigma_{BKG}$ is the sum over pixels in the local background region (for example, local background region 1041), $\text{bkg\_sig}(t_{FRAME}, x_{BKG}, y_{BKG})$ is the value of the background signal sample at time $(t_{FRAME})$ at pixel coordinates $(x_{BKG}, y_{BKG})$ located in the local background region, and $N_{BKG}$ is the number of pixels in the local background region.

In step 916, the average background signal value per frame is subtracted from the average ROI signal value per frame give a cell average ROI signal per frame, $\text{Cell\_ROI\_sig}(t_{FRAME})$, as follows:

$$\text{Cell\_avg\_ROI\_sig}(t_{FRAME}) = \text{Avg\_ROI\_sig}(t_{FRAME}) - \text{Avg\_bkg\_sig}(t_{FRAME}) \quad (10)$$

Referring to FIG. 10, the graph 1050 shows examples of plots of average ROI signals and average background signals. The plots 1051, 1052, 1053 and 1054 show the average ROI signal values for respective data acquisition time intervals. The plots 1061, 1062, 1063 and 1064 show the average background signal values for respective data acquisition time intervals. The plots 1051, 1061, 1052, 1062, 1053 and 1063 show the average ROI signal values and average background signal values in response to three flows of wash solution on the sensor array. The plots 1054 and 1064 show the average ROI signal values and average background signal values, respectively, determined for HepG2 cells in response to a flow of a reagent solution having an increasing concentration of FCCP on the sensor array. FCCP (carbonyl cyanide p-(tri-fluromethoxy)phenyl-hydrazone) is a potent uncoupler of oxidative phosphorylation in mitochondria. The concentration of FCCP was 1, 10 and 100 mM in the reagent solution (Thermo Fisher Live Cell Imaging Solution, Thermo Fisher Scientific, Cat. No. A14291DJ).

Figure 11A:
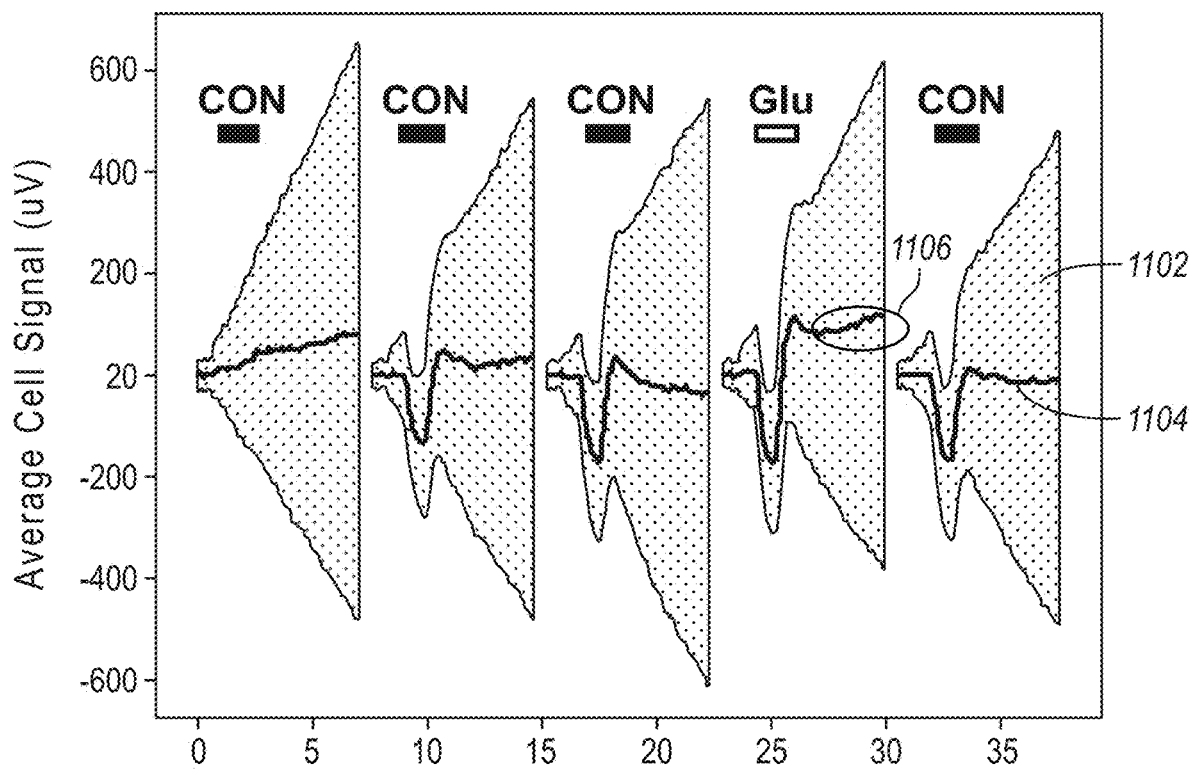
FIG. 11A gives examples of plots of the mean and standard deviation of average ROI signal values over time.
Figure 11B:
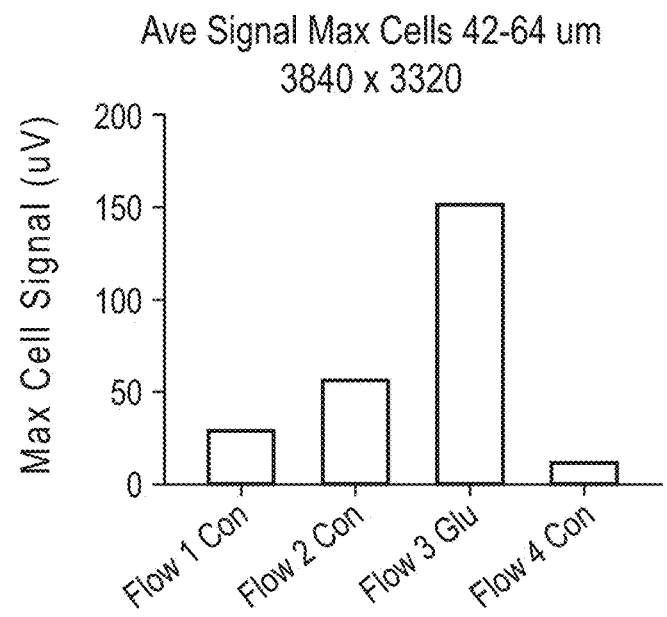
FIG. 11B shows an example of a bar graph of maximum values of average ROI signal values for multiple cells in the size range of 42-64 um.

Returning to FIG. 3, in step 308, the cell's average ROI signal values may be parameterized to analyze amplitude and time responses. For example, statistical parameters such as the mean, median, standard deviation of the cell's average ROI signal values over time may calculated. FIG. 11A gives examples of plots of the mean and standard deviation over time. The horizontal axis represent a time axis in seconds. The traces corresponding to acquisition periods, each having a 7 sec. duration are plotted. The time intervals between acquisition periods have been removed. The traces 1102 plot the +/−standard deviations and traces 104 plot the means. The means and standard deviations are plotted for responses to four flows of a control "CON" solution and one flow of a glucose "Glu" solution. The dips in the mean traces are transients as the solution flows past the cell. The mean trace in response to the glucose solution maintains an elevated steady state 1106 compared to the responses to the control solution flows. FIG. 11B shows an example of a bar graph of maximum values of average ROI signal values for multiple cells in the size range of 42-64 um. The results shown in FIG. 11A are a subset of the results shown in FIG. 11B.

Figure 12A:
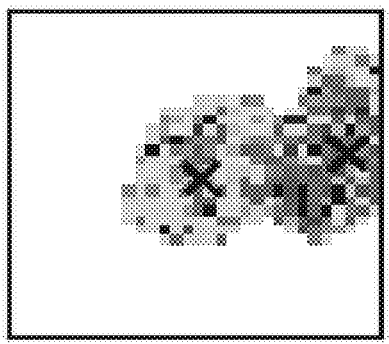
FIG. 12A shows an example of a spatial plot of the maximum amplitudes of the pixels in the cell regions over the acquisition time period.
Figure 12B:
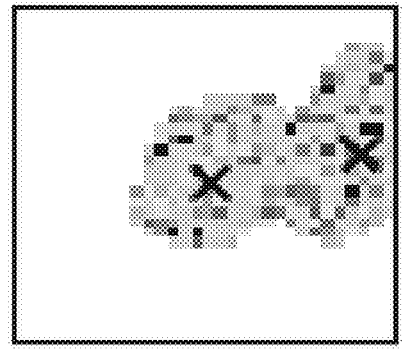
FIG. 12B shows an example of a spatial plot of the minimum amplitudes of the pixels in the cell regions over the acquisition time period.
Figure 12C:
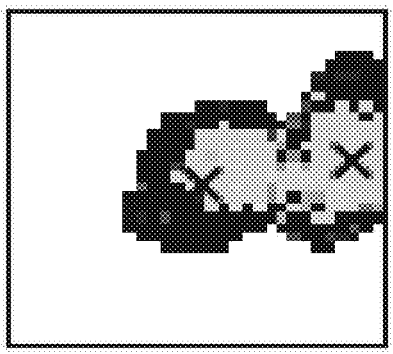
FIG. 12C shows an example of a spatial plot of the time to the peak value of the pixels in the cell regions over the acquisition time period.
Figure 12D:
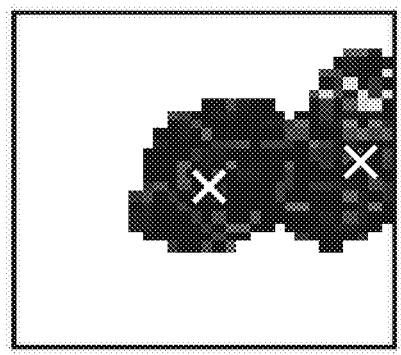
FIG. 12D shows an example of a spatial plot of the time to a trough value of the pixels in the cell regions over the acquisition time period.

FIGS. 12A-12D show examples of per pixel spatial plots of signal parameters for two cells. In these plots, the average local background is subtracted from the pixels in the cell regions as indicated in the final cell mask. The centroid for each cell is marked with an "X". FIG. 12A shows an example of a spatial plot of the maximum amplitudes of the pixels in the cell regions over the acquisition time period. FIG. 12B shows an example of a spatial plot of the minimum amplitudes of the pixels in the cell regions over the acquisition time period. FIG. 12C shows an example of a spatial plot of the time to the peak value of the pixels in the cell regions over the acquisition time period. FIG. 12D shows an example of a spatial plot of the time to a trough value of the pixels in the cell regions over the acquisition time period.

Figure 13:
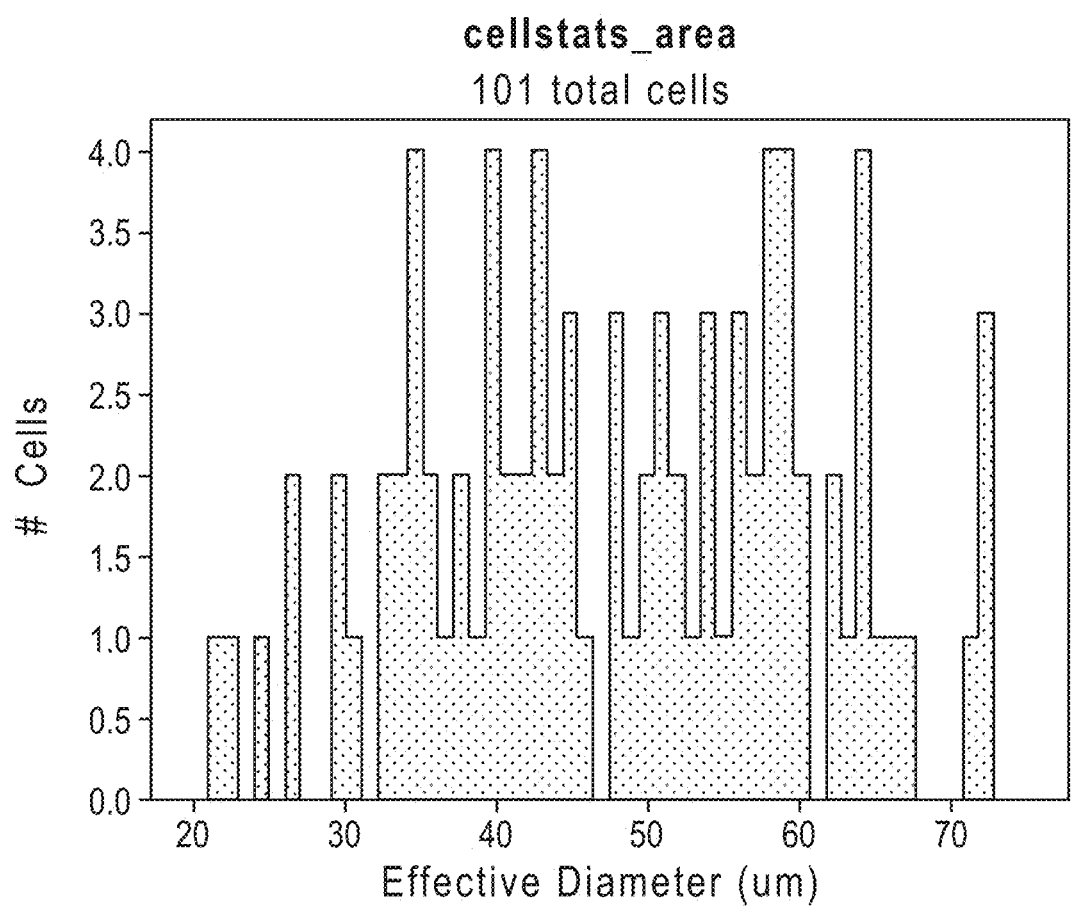
FIG. 13 gives examples of a histogram and statistics for cell sizes for 101 cells.

The final cell masks may be analyzed for cell size statistics. FIG. 13 gives examples of a histogram and statistics for cell sizes for 101 cells. The abbreviations q1, q2 and q3 indicate the first, second and third quartiles, respectively. The abbreviation "iqr" indicates the interquartile range, q3-q1, or middle half of the distribution. The effective diameter is described above with respect to equation (7).

According to various exemplary embodiments, one or more features of any one or more of the above-discussed teachings and/or exemplary embodiments may be performed or implemented using appropriately configured and/or programmed hardware and/or software elements. Determining whether an embodiment is implemented using hardware and/or software elements may be based on any number of factors, such as desired computational rate, power levels, heat tolerances, processing cycle budget, input data rates, output data rates, memory resources, data bus speeds, etc., and other design or performance constraints.

Examples of hardware elements may include processors, microprocessors, input(s) and/or output(s) (I/O) device(s) (or peripherals) that are communicatively coupled via a local interface circuit, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. The local interface may include, for example, one or more buses or other wired or wireless connections, controllers, buffers (caches), drivers, repeaters and receivers, etc., to allow appropriate communications between hardware components. A processor is a hardware device for executing software, particularly software stored in memory. The processor can be any custom made or commercially available processor, a central processing unit (CPU), an auxiliary processor among several processors associated with the computer, a semiconductor based microprocessor (e.g., in the form of a microchip or chip set), a macroprocessor, or generally any device for executing software instructions. A processor can also represent a distributed processing architecture. The I/O devices can include input devices, for example, a keyboard, a mouse, a scanner, a microphone, a touch screen, an interface for various medical devices and/or laboratory instruments, a bar code reader, a stylus, a laser reader, a radio-frequency device reader, etc. Furthermore, the I/O devices also can include output devices, for example, a printer, a bar code printer, a display, etc. Finally, the I/O devices further can include devices that communicate as both inputs and outputs, for example, a modulator/demodulator (modem; for accessing another device, system, or network), a radio frequency (RF) or other transceiver, a telephonic interface, a bridge, a router, etc.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. A software in memory may include one or more separate programs, which may include ordered listings of executable instructions for implementing logical functions. The software in memory may include a system for identifying data streams in accordance with the present teachings and any suitable custom made or commercially available operating system (O/S), which may control the execution of other computer programs such as the system, and provides scheduling, input-output control, file and data management, memory management, communication control, etc.

According to various exemplary embodiments, one or more features of any one or more of the above-discussed teachings and/or exemplary embodiments may be performed or implemented using appropriately configured and/or programmed non-transitory machine-readable medium or article that may store an instruction or a set of instructions that, if executed by a machine, may cause the machine to perform a method and/or operations in accordance with the exemplary embodiments. Such a machine may include, for example, any suitable processing platform, computing platform, computing device, processing device, computing system, processing system, computer, processor, scientific or laboratory instrument, etc., and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, read-only memory compact disc (CD-ROM), recordable compact disc (CD-R), rewriteable compact disc (CD-RW), optical disk, magnetic media, magneto-optical media, removable memory cards or disks, various types of Digital Versatile Disc (DVD), a tape, a cassette, etc., including any medium suitable for use in a computer. Memory can include any one or a combination of volatile memory elements (e.g., random access memory (RAM, such as DRAM, SRAM, SDRAM, etc.)) and non-volatile memory elements (e.g., ROM, EPROM, EEROM, Flash memory, hard drive, tape, CDROM, etc.). Moreover, memory can incorporate electronic, magnetic, optical, and/or other types of storage media. Memory can have a distributed architecture where various components are situated remote from one another, but are still accessed by the processor. The instructions may include any suitable type of code, such as source code, compiled code, interpreted code, executable code, static code, dynamic code, encrypted code, etc., implemented using any suitable high-level, low-level, object-oriented, visual, compiled and/or interpreted programming language.

According to various exemplary embodiments, one or more features of any one or more of the above-discussed teachings and/or exemplary embodiments may be performed or implemented at least partly using a distributed, clustered, remote, or cloud computing resource.

According to various exemplary embodiments, one or more features of any one or more of the above-discussed teachings and/or exemplary embodiments may be performed or implemented using a source program, executable program (object code), script, or any other entity comprising a set of instructions to be performed. When a source program, the program can be translated via a compiler, assembler, interpreter, etc., which may or may not be included within the memory, so as to operate properly in connection with the O/S. The instructions may be written using (a) an object oriented programming language, which has classes of data and methods, or (b) a procedural programming language, which has routines, subroutines, and/or functions, which may include, for example, C, C++, R, Pascal, Basic, Fortran, Cobol, Perl, Java, and Ada.

According to various exemplary embodiments, one or more of the above-discussed exemplary embodiments may include transmitting, displaying, storing, printing or outputting to a user interface device, a computer readable storage medium, a local computer system or a remote computer system, information related to any information, signal, data, and/or intermediate or final results that may have been generated, accessed, or used by such exemplary embodiments. Such transmitted, displayed, stored, printed or outputted information can take the form of searchable and/or filterable lists of runs and reports, pictures, tables, charts, graphs, spreadsheets, correlations, sequences, and combinations thereof, for example.

EXAMPLES

Example 1 is a method for analyzing cells disposed on a sensor array surface of a ChemFET sensor array device, including: flowing a solution having a step change in pH across the sensor array surface, wherein a plurality of ChemFET sensors of the ChemFET sensor array generate a plurality of signals in response to the step change in pH of the flowed solution to produce electroscopic image data; acquiring multiple frames of the electroscopic image data during an acquisition time interval, wherein each frame corresponds to signal samples of the plurality of signals generated by the ChemFET sensor array measured at a sampling time during the acquisition time interval, wherein each frame comprises a plurality of pixels, wherein a given pixel in the frame corresponds to a signal sample from a given sensor in the ChemFET sensor array; and segmenting the electroscopic image data into one or more cell regions corresponding to locations of the cells on the sensor array surface and one or more background regions corresponding to areas on the sensor array having no cells based on characteristics of the signal samples generated response to the step change in pH of the flowed solution.

Example 2 includes the subject matter of Example 1, and further specifies that each frame comprises a plurality of tiles, wherein each tile comprises a subset of pixels of the frame.

Example 3 includes the subject matter of Example 1, and further specifies that the segmenting step further includes subtracting a minimum pixel value from a maximum pixel value for each pixel location during the acquisition time interval to form a peak-to-peak image.

Example 4 includes the subject matter of Example 3, and further specifies that the segmenting step further includes calculating a mean value of pixels in the peak-to-peak image.

Example 5 includes the subject matter of Example 4, and further specifies that the segmenting step further includes subtracting the mean value from each pixel value in the peak-to-peak image to form a difference image.

Example 6 includes the subject matter of Example 5, and further specifies that the segmenting step further includes calculating an absolute value of each pixel in the difference image.

Example 7 includes the subject matter of Example 2, and further specifies that the segmenting step further includes calculating a mean value of pixels in the tile at each sampling time in the acquisition time interval to produce an array of mean values corresponding to each tile.

Example 8 includes the subject matter of Example 2, and further specifies that the segmenting step further includes dividing the tile into a plurality of sub-tiles.

Example 9 includes the subject matter of Example 8, and further specifies that the segmenting step further includes calculating a mean value of pixels in the sub-tile at each sampling time in the acquisition time interval to produce an array of mean values corresponding to each sub-tile.

Example 10 includes the subject matter of Example 9, and further specifies that the segmenting step further includes determining a frame index corresponding to a maximum mean value in the in the array of mean values Example 11 includes the subject matter of Example 2, and further specifies that the segmenting step further includes calculating an average over the acquisition time interval of each pixel value in the tile to form a first average image.

Example 12 includes the subject matter of Example 11, and further specifies that the segmenting step further includes calculating an average over a plurality of initial frames in the acquisition time interval of each pixel value in the tile to form a second average image.

Example 13 includes the subject matter of Example 12, and further specifies that the segmenting step further includes subtracting the second average image from the first average image to form a temporal average image.

Example 14 includes the subject matter of Example 1, and further specifies that the segmenting step further includes determining a maximum pixel value during the acquisition time interval for each pixel location.

Example 15 includes the subject matter of Example 14, and further specifies that the segmenting step further includes determining a frame index corresponding to the maximum pixel value.

Example 16 includes the subject matter of Example 14, and further specifies that the segmenting step further includes determining a frame index corresponding to 80% of the maximum pixel value.

Example 17 includes the subject matter of Example 2, and further specifies that the segmenting step further includes determining feature values based on the characteristics of the signal samples corresponding to each pixel of the tile to form a CellFind image.

Example 18 includes the subject matter of Example 17, and further specifies that the segmenting step further includes applying a blurring function to the CellFind image to form a blurred CellFind image.

Example 19 includes the subject matter of Example 18, and further specifies that the blurring function comprises applying a low-pass filter to the CellFind image in a frequency domain.

Example 20 includes the subject matter of Example 18, and further specifies that the segmenting step further includes applying a threshold to pixels of the blurred CellFind image to produce a coarse cell mask, wherein pixel values greater than or equal to the threshold are assigned a value of 1 and pixel values less than the threshold are assigned a value of 0.

Example 21 includes the subject matter of Example 20, and further specifies that the segmenting step further includes filtering the coarse cell mask to select features of the coarse cell mask having sizes of interest to form a filtered cell mask.

Example 22 includes the subject matter of Example 21, and further specifies that the sizes of interest correspond to sizes of cells.

Example 23 includes the subject matter of Example 21, and further specifies that the segmenting step further includes applying a watershed algorithm to the selected features of the filtered cell mask to classify pixels of the filtered cell mask into one or more initial cell regions and one or more initial background regions to form a cell mask.

Example 24 includes the subject matter of Example 23, and further specifies that the segmenting step further includes verifying the cell mask based on Pearson Differences calculated between a cell average time series and a cell and background time series for a nearest sub-region in the cell mask.

Example 25 includes the subject matter of Example 24, and further specifies that the segmenting step further includes clustering the Pearson Differences to determine the cell regions and the background regions for a final cell mask.

Example 26 includes the subject matter of Example 2, and further specifies that the segmenting step further includes determining a plurality of feature values based on a plurality of different characteristics of the signal samples corresponding to each pixel of the tile to form a plurality of CellFind images.

Example 27 includes the subject matter of Example 26, and further specifies that the segmenting step further includes applying a blurring function to each of the plurality of CellFind images to form a plurality of blurred CellFind images.

Example 28 includes the subject matter of Example 27, and further specifies that the segmenting step further includes applying a respective threshold to each of the plurality of blurred CellFind images to produce a plurality of coarse cell masks, wherein pixel values greater than or equal to the respective threshold are assigned a value of 1 and pixel values less than the respective threshold are assigned a value of 0.

Example 29 includes the subject matter of Example 28, and further specifies that the segmenting sum image.

Example 30 includes the subject matter of Example 29, and further specifies that the segmenting step further includes applying a second threshold to the weighted sum image to form a consensus cell mask, wherein pixel values greater than or equal to the second threshold are assigned a value of 1 and pixel values less than the second threshold are assigned a value of 0.

Example 31 includes the subject matter of Example 30, and further specifies that the segmenting step further includes filtering the consensus cell mask to select features of the consensus cell mask having sizes of interest to form a filtered cell mask.

Example 32 includes the subject matter of Example 31, and further specifies that the sizes of interest correspond to sizes of cells.

Example 33 includes the subject matter of Example 31, and further specifies that the segmenting step further includes applying a watershed algorithm to the selected features of the filtered cell mask to classify pixels of the filtered cell mask into one or more initial cell regions and one or more initial background regions to form a cell mask.

Example 34 includes the subject matter of Example 33, and further specifies that the segmenting step further includes verifying the cell mask based on Pearson Differences calculated between a cell average time series and a cell and background time series for a nearest sub-region in the cell mask.

Example 35 includes the subject matter of Example 34, and further specifies that the segmenting step further includes clustering the Pearson Differences to determine the cell regions and the background regions for a final cell mask.

Example 36 is a system for analyzing cells disposed on a sensor array surface of a ChemFET sensor array device, including a processor and a data store communicatively connected with the processor, the processor configured to execute instructions, which, when executed by the processor, cause the system to perform a method, including: acquiring multiple frames of the electroscopic image data during an acquisition time interval, wherein the electroscopic image data is produced in response to flowing a solution having a step change in pH across the sensor array surface, wherein a plurality of ChemFET sensors of the ChemFET sensor array generate a plurality of signals in response to the step change in pH of the flowed solution to produce the electroscopic image data, wherein each frame corresponds to signal samples of the plurality of signals generated by the ChemFET sensor array measured at a sampling time during the acquisition time interval, wherein each frame comprises a plurality of pixels, wherein a given pixel in the frame corresponds to a signal sample from a given sensor in the ChemFET sensor array; and segmenting the electroscopic image data into one or more cell regions corresponding to locations of the cells on the sensor array surface and one or more background regions corresponding to areas on the sensor array having no cells based on characteristics of the signal samples generated response to the step change in pH of the flowed solution.

Example 37 includes the subject matter of Example 36, and further specifies that each frame comprises a plurality of tiles, wherein each tile comprises a subset of pixels of the frame.

Example 38 includes the subject matter of Example 36, and further specifies that the segmenting step further includes subtracting a minimum pixel value from a maximum pixel value for each pixel location during the acquisition time interval to form a peak-to-peak image.

Example 39 includes the subject matter of Example 38, and further specifies that the segmenting step further includes calculating a mean value of pixels in the peak-to-peak image.

Example 40 includes the subject matter of Example 39, and further specifies that the segmenting step further includes subtracting the mean value from each pixel value in the peak-to-peak image to form a difference image.

Example 41 includes the subject matter of Example 40, and further specifies that the segmenting step further includes calculating an absolute value of each pixel in the difference image.

Example 42 includes the subject matter of Example 37, and further specifies that the segmenting step further includes calculating a mean value of pixels in the tile at each sampling time in the acquisition time interval to produce an array of mean values corresponding to each tile.

Example 43 includes the subject matter of Example 37, and further specifies that the segmenting step further includes dividing the tile into a plurality of sub-tiles.

Example 44 includes the subject matter of Example 43, and further specifies that the segmenting step further includes calculating a mean value of pixels in the sub-tile at each sampling time in the acquisition time interval to produce an array of mean values corresponding to each sub-tile.

Example 45 includes the subject matter of Example 44, and further specifies that the segmenting step further includes determining a frame index corresponding to a maximum mean value in the in the array of mean values Example 46 includes the subject matter of Example 37, and further specifies that the segmenting step further includes calculating an average over the acquisition time interval of each pixel value in the tile to form a first average image.

Example 47 includes the subject matter of Example 46, and further specifies that the segmenting step further includes calculating an average over a plurality of initial frames in the acquisition time interval of each pixel value in the tile to form a second average image.

Example 48 includes the subject matter of Example 47, and further specifies that the segmenting step further includes subtracting the second average image from the first average image to form a temporal average image.

Example 49 includes the subject matter of Example 36, and further specifies that the segmenting step further includes determining a maximum pixel value during the acquisition time interval for each pixel location.

Example 50 includes the subject matter of Example 49, and further specifies that the segmenting step further includes determining a frame index corresponding to the maximum pixel value.

Example 51 includes the subject matter of Example 49, and further specifies that the segmenting step further includes determining a frame index corresponding to 80% of the maximum pixel value.

Example 52 includes the subject matter of Example 37, and further specifies that the segmenting step further includes determining feature values based on the characteristics of the signal samples corresponding to each pixel of the tile to form a CellFind image.

Example 53 includes the subject matter of Example 52, and further specifies that the segmenting step further includes applying a blurring function to the CellFind image to form a blurred CellFind image.

Example 54 includes the subject matter of Example 53, and further specifies that the blurring function comprises applying a low-pass filter to the CellFind image in a frequency domain.

Example 55 includes the subject matter of Example 53, and further specifies that the segmenting step further includes applying a threshold to pixels of the blurred CellFind image to produce a coarse cell mask, wherein pixel values greater than or equal to the threshold are assigned a value of 1 and pixel values less than the threshold are assigned a value of 0.

Example 56 includes the subject matter of Example 55, and further specifies that the segmenting step further includes filtering the coarse cell mask to select features of the coarse cell mask having sizes of interest to form a filtered cell mask.

Example 57 includes the subject matter of Example 56, and further specifies that the sizes of interest correspond to sizes of cells.

Example 58 includes the subject matter of Example 56, and further specifies that the segmenting step further includes applying a watershed algorithm to the selected features of the filtered cell mask to classify pixels of the filtered cell mask into one or more initial cell regions and one or more initial background regions to form a cell mask.

Example 59 includes the subject matter of Example 58, and further specifies that the segmenting step further includes verifying the cell mask based on Pearson Differences calculated between a cell average time series and a cell and background time series for a nearest sub-region in the cell mask.

Example 60 includes the subject matter of Example 59, and further specifies that the segmenting step further includes clustering the Pearson Differences to determine the cell regions and the background regions for a final cell mask.

Example 61 includes the subject matter of Example 37, and further specifies that the segmenting step further includes determining a plurality of feature values based on a plurality of different characteristics of the signal samples corresponding to each pixel of the tile to form a plurality of CellFind images.

Example 62 includes the subject matter of Example 61, and further specifies that the segmenting step further includes applying a blurring function to each of the plurality of CellFind images to form a plurality of blurred CellFind images.

Example 63 includes the subject matter of Example 62, and further specifies that the segmenting step further includes applying a respective threshold to each of the plurality of blurred CellFind images to produce a plurality of coarse cell masks, wherein pixel values greater than or equal to the respective threshold are assigned a value of 1 and pixel values less than the respective threshold are assigned a value of 0.

Example 64 includes the subject matter of Example 63, and further specifies that the segmenting sum image.

Example 65 includes the subject matter of Example 64, and further specifies that the segmenting step further includes applying a second threshold to the weighted sum image to form a consensus cell mask, wherein pixel values greater than or equal to the second threshold are assigned a value of 1 and pixel values less than the second threshold are assigned a value of 0.

Example 66 includes the subject matter of Example 65, and further specifies that the segmenting step further includes filtering the consensus cell mask to select features of the consensus cell mask having sizes of interest to form a filtered cell mask.

Example 67 includes the subject matter of Example 66, and further specifies that the sizes of interest correspond to sizes of cells.

Example 68 includes the subject matter of Example 66, and further specifies that the segmenting step further includes applying a watershed algorithm to the selected features of the filtered cell mask to classify pixels of the filtered cell mask into one or more initial cell regions and one or more initial background regions to form a cell mask.

Example 69 includes the subject matter of Example 68, and further specifies that the segmenting step further includes verifying the cell mask based on Pearson Differences calculated between a cell average time series and a cell and background time series for a nearest sub-region in the cell mask.

Example 70 includes the subject matter of Example 69, and further specifies that the segmenting step further includes clustering the Pearson Differences to determine the cell regions and the background regions for a final cell mask.

Example 71 is a non-transitory computer-readable medium storing instructions that, when executed by a computer, cause the computer to perform a method for analyzing cells disposed on a sensor array surface of a ChemFET sensor array device, the method comprising: acquiring multiple frames of electroscopic image data during an acquisition time interval, wherein the electroscopic image data is produced in response to flowing a solution having a step change in pH across the sensor array surface, wherein a plurality of ChemFET sensors of the ChemFET sensor array generate a plurality of signals in response to the step change in pH of the flowed solution to produce the electroscopic image data, wherein each frame corresponds to signal samples of the plurality of signals generated by the ChemFET sensor array measured at a sampling time during the acquisition time interval, wherein each frame comprises a plurality of pixels, wherein a given pixel in the frame corresponds to a signal sample from a given sensor in the ChemFET sensor array; and segmenting the electroscopic image data into one or more cell regions corresponding to locations of the cells on the sensor array surface and one or more background regions corresponding to areas on the sensor array having no cells based on characteristics of the signal samples generated response to the step change in pH of the flowed solution.

Example 72 includes the subject matter of Example 71, and further specifies that each frame comprises a plurality of tiles, wherein each tile comprises a subset of pixels of the frame.

Example 73 includes the subject matter of Example 71, and further specifies that the segmenting step further includes subtracting a minimum pixel value from a maximum pixel value for each pixel location during the acquisition time interval to form a peak-to-peak image.

Example 74 includes the subject matter of Example 73, and further specifies that the segmenting step further includes calculating a mean value of pixels in the peak-to-peak image.

Example 75 includes the subject matter of Example 74, and further specifies that the segmenting step further includes subtracting the mean value from each pixel value in the peak-to-peak image to form a difference image.

Example 76 includes the subject matter of Example 75, and further specifies that the segmenting step further includes calculating an absolute value of each pixel in the difference image.

Example 77 includes the subject matter of Example 72, and further specifies that the segmenting step further includes calculating a mean value of pixels in the tile at each sampling time in the acquisition time interval to produce an array of mean values corresponding to each tile.

Example 78 includes the subject matter of Example 72, and further specifies that the segmenting step further includes dividing the tile into a plurality of sub-tiles.

Example 79 includes the subject matter of Example 78, and further specifies that the segmenting step further includes calculating a mean value of pixels in the sub-tile at each sampling time in the acquisition time interval to produce an array of mean values corresponding to each sub-tile.

Example 80 includes the subject matter of Example 79, and further specifies that the segmenting step further includes determining a frame index corresponding to a maximum mean value in the in the array of mean values Example 81 includes the subject matter of Example 72, and further specifies that the segmenting step further includes calculating an average over the acquisition time interval of each pixel value in the tile to form a first average image.

Example 82 includes the subject matter of Example 81, and further specifies that the segmenting step further includes calculating an average over a plurality of initial frames in the acquisition time interval of each pixel value in the tile to form a second average image.

Example 83 includes the subject matter of Example 82, and further specifies that the segmenting step further includes subtracting the second average image from the first average image to form a temporal average image.

Example 84 includes the subject matter of Example 71, and further specifies that the segmenting step further includes determining a maximum pixel value during the acquisition time interval for each pixel location.

Example 85 includes the subject matter of Example 84, and further specifies that the segmenting step further includes determining a frame index corresponding to the maximum pixel value.

Example 86 includes the subject matter of Example 84, and further specifies that the segmenting step further includes determining a frame index corresponding to 80% of the maximum pixel value.

Example 87 includes the subject matter of Example 72, and further specifies that the segmenting step further includes determining feature values based on the characteristics of the signal samples corresponding to each pixel of the tile to form a CellFind image.

Example 88 includes the subject matter of Example 87, and further specifies that the segmenting step further includes applying a blurring function to the CellFind image to form a blurred CellFind image.

Example 89 includes the subject matter of Example 88, and further specifies that the blurring function comprises applying a low-pass filter to the CellFind image in a frequency domain.

Example 90 includes the subject matter of Example 88, and further specifies that the segmenting step further includes applying a threshold to pixels of the blurred CellFind image to produce a coarse cell mask, wherein pixel values greater than or equal to the threshold are assigned a value of 1 and pixel values less than the threshold are assigned a value of 0.

Example 91 includes the subject matter of Example 90, and further specifies that the segmenting step further includes filtering the coarse cell mask to select features of the coarse cell mask having sizes of interest to form a filtered cell mask.

Example 92 includes the subject matter of Example 91, and further specifies that the sizes of interest correspond to sizes of cells.

Example 93 includes the subject matter of Example 91, and further specifies that the segmenting step further includes applying a watershed algorithm to the selected features of the filtered cell mask to classify pixels of the filtered cell mask into one or more initial cell regions and one or more initial background regions to form a cell mask.

Example 94 includes the subject matter of Example 93, and further specifies that the segmenting step further includes verifying the cell mask based on Pearson Differences calculated between a cell average time series and a cell and background time series for a nearest sub-region in the cell mask.

Example 95 includes the subject matter of Example 94, and further specifies that the segmenting step further includes clustering the Pearson Differences to determine the cell regions and the background regions for a final cell mask.

Example 96 includes the subject matter of Example 72, and further specifies that the segmenting step further includes determining a plurality of feature values based on a plurality of different characteristics of the signal samples corresponding to each pixel of the tile to form a plurality of CellFind images.

Example 97 includes the subject matter of Example 96, and further specifies that the segmenting step further includes applying a blurring function to each of the plurality of CellFind images to form a plurality of blurred CellFind images.

Example 98 includes the subject matter of Example 97, and further specifies that the segmenting step further includes applying a respective threshold to each of the plurality of blurred CellFind images to produce a plurality of coarse cell masks, wherein pixel values greater than or equal to the respective threshold are assigned a value of 1 and pixel values less than the respective threshold are assigned a value of 0.

Example 99 includes the subject matter of Example 98, and further specifies that the segmenting sum image.

Example 100 includes the subject matter of Example 99, and further specifies that the segmenting step further includes applying a second threshold to the weighted sum image to form a consensus cell mask, wherein pixel values greater than or equal to the second threshold are assigned a value of 1 and pixel values less than the second threshold are assigned a value of 0.

Example 101 includes the subject matter of Example 100, and further specifies that the segmenting step further includes filtering the consensus cell mask to select features of the consensus cell mask having sizes of interest to form a filtered cell mask.

Example 102 includes the subject matter of Example 101, and further specifies that the sizes of interest correspond to sizes of cells.

Example 103 includes the subject matter of Example 101, and further specifies that the segmenting step further includes applying a watershed algorithm to the selected features of the filtered cell mask to classify pixels of the filtered cell mask into one or more initial cell regions and one or more initial background regions to form a cell mask.

Example 104 includes the subject matter of Example 103, and further specifies that the segmenting step further includes verifying the cell mask based on Pearson Differences calculated between a cell average time series and a cell and background time series for a nearest sub-region in the cell mask.

Example 105 includes the subject matter of Example 104, and further specifies that the segmenting step further includes clustering the Pearson Differences to determine the cell regions and the background regions for a final cell mask.

Example A1 is a method for analyzing cells disposed on a sensor array surface of a ChemFET sensor array device, including: flowing a solution having a step change in pH across the sensor array surface, wherein a plurality of ChemFET sensors of the ChemFET sensor array generate a plurality of signals in response to the step change in pH of the flowed solution to produce electroscopic image data; acquiring multiple frames of the electroscopic image data during an acquisition time interval, wherein each frame corresponds to signal samples of the plurality of signals generated by the ChemFET sensor array measured at a sampling time during the acquisition time interval, wherein each frame comprises a plurality of pixels, wherein a given pixel in the frame corresponds to a signal sample from a given sensor in the ChemFET sensor array; and segmenting the electroscopic image data into one or more cell regions corresponding to locations of the cells on the sensor array surface and one or more background regions corresponding to areas on the sensor array having no cells based on characteristics of the signal samples generated response to the step change in pH of the flowed solution.

Example A2 includes the subject matter of Example A1, and further specifies that each frame comprises a plurality of tiles, wherein each tile comprises a subset of pixels of the frame.

Example A3 includes the subject matter of Example A1, and further specifies that the segmenting step further includes subtracting a minimum pixel value from a maximum pixel value for each pixel location during the acquisition time interval to form a peak-to-peak image.

Example A4 includes the subject matter of Example A3, and further specifies that the segmenting step further includes: calculating a mean value of pixels in the peak-to-peak image; subtracting the mean value from each pixel value in the peak-to-peak image to form a difference image; and calculating an absolute value of each pixel in the difference image.

Example A5 includes the subject matter of Example A2, and further specifies that the segmenting step further includes determining feature values based on the characteristics of the signal samples corresponding to each pixel of the tile to form a CellFind image.

Example A6 includes the subject matter of Example A5, and further specifies that the segmenting step further includes applying a blurring function to the CellFind image to form a blurred CellFind image, wherein the blurring function comprises applying a low-pass filter to the CellFind image.

Example A7 includes the subject matter of Example A6, and further specifies that the segmenting step further includes applying a threshold to pixels of the blurred CellFind image to produce a coarse cell mask, wherein pixel values greater than or equal to the threshold are assigned a value of 1 and pixel values less than the threshold are assigned a value of 0.

Example A8 includes the subject matter of Example A7, and further specifies that the segmenting step further includes filtering the coarse cell mask to select features of the coarse cell mask having sizes of interest to form a filtered cell mask.

Example A9 includes the subject matter of Example A8, and further specifies that the segmenting step further includes applying a watershed algorithm to the selected features of the filtered cell mask to classify pixels of the filtered cell mask into one or more initial cell regions and one or more initial background regions to form a cell mask.

Example A10 includes the subject matter of Example A9, and further specifies that the segmenting step further includes: verifying the cell mask based on Pearson Differences calculated between a cell average time series and a cell and background time series for a nearest sub-region in the cell mask; and clustering the Pearson Differences to determine the cell regions and the background regions for a final cell mask.

Example A11 is a system for analyzing cells disposed on a sensor array surface of a ChemFET sensor array device, including a processor and a data store communicatively connected with the processor, the processor configured to execute instructions, which, when executed by the processor, cause the system to perform a method, including: acquiring multiple frames of electroscopic image data during an acquisition time interval, wherein the electroscopic image data is produced in response to flowing a solution having a step change in pH across the sensor array surface, wherein a plurality of ChemFET sensors of the ChemFET sensor array generate a plurality of signals in response to the step change in pH of the flowed solution to produce the electroscopic image data, wherein each frame corresponds to signal samples of the plurality of signals generated by the ChemFET sensor array measured at a sampling time during the acquisition time interval, wherein each frame comprises a plurality of pixels, wherein a given pixel in the frame corresponds to a signal sample from a given sensor in the ChemFET sensor array; and segmenting the electroscopic image data into one or more cell regions corresponding to locations of the cells on the sensor array surface and one or more background regions corresponding to areas on the sensor array having no cells based on characteristics of the signal samples generated response to the step change in pH of the flowed solution.

Example A12 includes the subject matter of Example A11, and further specifies that each frame comprises a plurality of tiles, wherein each tile comprises a subset of pixels of the frame.

Example A13 includes the subject matter of Example A11, and further specifies that the segmenting step further includes subtracting a minimum pixel value from a maximum pixel value for each pixel location during the acquisition time interval to form a peak-to-peak image.

Example A14 includes the subject matter of Example A13, and further specifies that the segmenting step further includes: calculating a mean value of pixels in the peak-to-peak image; subtracting the mean value from each pixel value in the peak-to-peak image to form a difference image; and calculating an absolute value of each pixel in the difference image.

Example A15 includes the subject matter of Example A12, and further specifies that the segmenting step further includes determining feature values based on the characteristics of the signal samples corresponding to each pixel of the tile to form a CellFind image.

Example A16 includes the subject matter of Example A15, and further specifies that the segmenting step further includes applying a blurring function to the CellFind image to form a blurred CellFind image, wherein the blurring function comprises applying a low-pass filter to the CellFind image.

Example A17 includes the subject matter of Example A16, and further specifies that the segmenting step further includes applying a threshold to pixels of the blurred CellFind image to produce a coarse cell mask, wherein pixel values greater than or equal to the threshold are assigned a value of 1 and pixel values less than the threshold are assigned a value of 0.

Example A18 includes the subject matter of Example A17, and further specifies that the segmenting step further includes filtering the coarse cell mask to select features of the coarse cell mask having sizes of interest to form a filtered cell mask.

Example A19 includes the subject matter of Example A18, and further specifies that the segmenting step further includes applying a watershed algorithm to the selected features of the filtered cell mask to classify pixels of the filtered cell mask into one or more initial cell regions and one or more initial background regions to form a cell mask.

Example A20 includes the subject matter of Example A19, and further specifies that the segmenting step further includes: verifying the cell mask based on Pearson Differences calculated between a cell average time series and a cell and background time series for a nearest sub-region in the cell mask; and clustering the Pearson Differences to determine the cell regions and the background regions for a final cell mask.

Example A21 is a non-transitory computer-readable medium storing instructions that, when executed by a computer, cause the computer to perform a method for analyzing cells disposed on a sensor array surface of a ChemFET sensor array device, the method comprising: acquiring multiple frames of electroscopic image data during an acquisition time interval, wherein the electroscopic image data is produced in response to flowing a solution having a step change in pH across the sensor array surface, wherein a plurality of ChemFET sensors of the ChemFET sensor array generate a plurality of signals in response to the step change in pH of the flowed solution to produce the electroscopic image data, wherein each frame corresponds to signal samples of the plurality of signals generated by the ChemFET sensor array measured at a sampling time during the acquisition time interval, wherein each frame comprises a plurality of pixels, wherein a given pixel in the frame corresponds to a signal sample from a given sensor in the ChemFET sensor array; and segmenting the electroscopic image data into one or more cell regions corresponding to locations of the cells on the sensor array surface and one or more background regions corresponding to areas on the sensor array having no cells based on characteristics of the signal samples generated response to the step change in pH of the flowed solution.

Example A22 includes the subject matter of Example A21, and further specifies that each frame comprises a plurality of tiles, wherein each tile comprises a subset of pixels of the frame.

Example A23 includes the subject matter of Example A21, and further specifies that the segmenting step further includes subtracting a minimum pixel value from a maximum pixel value for each pixel location during the acquisition time interval to form a peak-to-peak image.

Example A24 includes the subject matter of Example A23, and further specifies that the segmenting step further includes: calculating a mean value of pixels in the peak-to-peak image; subtracting the mean value from each pixel value in the peak-to-peak image to form a difference image; and calculating an absolute value of each pixel in the difference image.

Example A25 includes the subject matter of Example A22, and further specifies that the segmenting step further includes determining feature values based on the characteristics of the signal samples corresponding to each pixel of the tile to form a CellFind image.

Example A26 includes the subject matter of Example A25, and further specifies that the segmenting step further includes applying a blurring function to the CellFind image to form a blurred CellFind image, wherein the blurring function comprises applying a low-pass filter to the CellFind image.

Example A27 includes the subject matter of Example A26, and further specifies that the segmenting step further includes applying a threshold to pixels of the blurred CellFind image to produce a coarse cell mask, wherein pixel values greater than or equal to the threshold are assigned a value of 1 and pixel values less than the threshold are assigned a value of 0.

Example A28 includes the subject matter of Example A27, and further specifies that the segmenting step further includes filtering the coarse cell mask to select features of the coarse cell mask having sizes of interest to form a filtered cell mask.

Example A29 includes the subject matter of Example A28, and further specifies that the segmenting step further includes applying a watershed algorithm to the selected features of the filtered cell mask to classify pixels of the filtered cell mask into one or more initial cell regions and one or more initial background regions to form a cell mask.

Example A30 includes the subject matter of Example A29, and further specifies that the segmenting step further includes: verifying the cell mask based on Pearson Differences calculated between a cell average time series and a cell and background time series for a nearest sub-region in the cell mask; and clustering the Pearson Differences to determine the cell regions and the background regions for a final cell mask.

What is claimed is:

1. A method for analyzing cells disposed on a sensor array surface of a ChemFET sensor array device, comprising:
    flowing a solution having a step change in pH across the sensor array surface, wherein a plurality of ChemFET sensors of the ChemFET sensor array generate a plurality of signals in response to the step change in pH of the flowed solution to produce electroscopic image data;
    acquiring multiple frames of the electroscopic image data during an acquisition time interval, wherein each frame corresponds to signal samples of the plurality of signals generated by the ChemFET sensor array measured at a sampling time during the acquisition time interval, wherein each frame comprises a plurality of pixels, wherein a given pixel in the frame corresponds to a signal sample from a given sensor in the ChemFET sensor array; and
    segmenting the electroscopic image data into one or more cell regions corresponding to locations of the cells on the sensor array surface and one or more background regions corresponding to areas on the sensor array having no cells based on characteristics of the signal samples generated response to the step change in pH of the flowed solution.

2. The method of claim 1, wherein each frame comprises a plurality of tiles, wherein each tile comprises a subset of pixels of the frame.

3. The method of claim 1, wherein the segmenting step further includes subtracting a minimum pixel value from a maximum pixel value for each pixel location during the acquisition time interval to form a peak-to-peak image.

4. The method of claim 3, wherein the segmenting step further includes:
    calculating a mean value of pixels in the peak-to-peak image;
    subtracting the mean value from each pixel value in the peak-to-peak image to form a difference image; and
    calculating an absolute value of each pixel in the difference image.

5. The method of claim 2, wherein the segmenting step further includes determining feature values based on the characteristics of the signal samples corresponding to each pixel of the tile to form a CellFind image.

6. The method of claim 5, wherein the segmenting step further includes applying a blurring function to the CellFind image to form a blurred CellFind image, wherein the blurring function comprises applying a low-pass filter to the CellFind image.

7. The method of claim 6, wherein the segmenting step further includes applying a threshold to pixels of the blurred CellFind image to produce a coarse cell mask, wherein pixel values greater than or equal to the threshold are assigned a value of 1 and pixel values less than the threshold are assigned a value of 0.

8. The method of claim 7, wherein the segmenting step further includes filtering the coarse cell mask to select features of the coarse cell mask having sizes of interest to form a filtered cell mask.

9. The method of claim 8, wherein the segmenting step further includes applying a watershed algorithm to the selected features of the filtered cell mask to classify pixels of the filtered cell mask into one or more initial cell regions and one or more initial background regions to form a cell mask.

10. The method of claim 9, wherein the segmenting step further includes:
    verifying the cell mask based on Pearson Differences calculated between a cell average time series and a cell and background time series for a nearest sub-region in the cell mask; and
    clustering the Pearson Differences to determine the cell regions and the background regions for a final cell mask.

11. A system for analyzing cells disposed on a sensor array surface of a ChemFET sensor array device, comprising a processor and a data store communicatively connected with the processor, the processor configured to execute instructions, which, when executed by the processor, cause the system to perform a method, including:
    acquiring multiple frames of electroscopic image data during an acquisition time interval, wherein the electroscopic image data is produced in response to flowing a solution having a step change in pH across the sensor array surface, wherein a plurality of ChemFET sensors of the ChemFET sensor array generate a plurality of signals in response to the step change in pH of the flowed solution to produce the electroscopic image data, wherein each frame corresponds to signal samples of the plurality of signals generated by the ChemFET sensor array measured at a sampling time during the acquisition time interval, wherein each frame comprises a plurality of pixels, wherein a given pixel in the frame corresponds to a signal sample from a given sensor in the ChemFET sensor array; and
    segmenting the electroscopic image data into one or more cell regions corresponding to locations of the cells on the sensor array surface and one or more background regions corresponding to areas on the sensor array having no cells based on characteristics of the signal samples generated response to the step change in pH of the flowed solution.

12. The system of claim 11, wherein each frame comprises a plurality of tiles, wherein each tile comprises a subset of pixels of the frame.

13. The system of claim 11, wherein the segmenting step further includes subtracting a minimum pixel value from a maximum pixel value for each pixel location during the acquisition time interval to form a peak-to-peak image.

14. The system of claim 13, wherein the segmenting step further includes:
    calculating a mean value of pixels in the peak-to-peak image;
    subtracting the mean value from each pixel value in the peak-to-peak image to form a difference image; and
    calculating an absolute value of each pixel in the difference image.

15. The system of claim 12, wherein the segmenting step further includes determining feature values based on the characteristics of the signal samples corresponding to each pixel of the tile to form a CellFind image.

16. The system of claim 15, wherein the segmenting step further includes applying a blurring function to the CellFind image to form a blurred CellFind image, wherein the blurring function comprises applying a low-pass filter to the CellFind image.

17. The system of claim 16, wherein the segmenting step further includes applying a threshold to pixels of the blurred CellFind image to produce a coarse cell mask, wherein pixel values greater than or equal to the threshold are assigned a value of 1 and pixel values less than the threshold are assigned a value of 0.

18. The system of claim 17, wherein the segmenting step further includes filtering the coarse cell mask to select features of the coarse cell mask having sizes of interest to form a filtered cell mask.

19. The system of claim 18, wherein the segmenting step further includes applying a watershed algorithm to the selected features of the filtered cell mask to classify pixels of the filtered cell mask into one or more initial cell regions and one or more initial background regions to form a cell mask.

20. The system of claim 19, wherein the segmenting step further includes:
   verifying the cell mask based on Pearson Differences calculated between a cell average time series and a cell and background time series for a nearest sub-region in the cell mask; and
   clustering the Pearson Differences to determine the cell regions and the background regions for a final cell mask.

* * * * *